US007381693B2

(12) United States Patent
Keenan et al.

(10) Patent No.: US 7,381,693 B2

(45) **Date of Patent: *Jun. 3, 2008**

(54) FIBROUS ELASTIC GEL CLEANSING ARTICLE

(75) Inventors: Diane Marie Keenan, Derby, CT (US); Gregory Aaron Grissett, Jacksonville, NC (US); Filomena Augusta Macedo, Naugatuck, CT (US); David Robert Williams, Monroe, CT (US)

(73) Assignee: Unilever Home & Personal Care USA, divison of Conopco, Inc., Greenwich, CT (US)

( * ) Notice: Subject to any disclaimer, the term of this patent is extended or adjusted under 35 U.S.C. 154(b) by 312 days.

This patent is subject to a terminal disclaimer.

(21) Appl. No.: 11/023,207

(22) Filed: Dec. 27, 2004

(65) Prior Publication Data

US 2005/0277568 A1 Dec. 15, 2005

Related U.S. Application Data

(60) Provisional application No. 60/579,592, filed on Jun. 14, 2004.

(51) Int. Cl.
*A61K 7/50* (2006.01)

(52) U.S. Cl. ...................... 510/141; 510/144; 510/146; 510/156

(58) Field of Classification Search ..................... None
See application file for complete search history.

(56) References Cited

U.S. PATENT DOCUMENTS

| | | | | |
|---|---|---|---|---|
| 3,949,137 | A | 4/1976 | Akrongold et al. | |
| 4,181,632 | A | 1/1980 | Schebece | |
| 4,190,550 | A | 2/1980 | Campbell | |
| 4,207,198 | A | 6/1980 | Kenkare | |
| 4,328,131 | A | 5/1982 | Carson, Jr. et al. | |
| 4,613,446 | A | 9/1986 | Magyar | |
| 4,969,225 | A | 11/1990 | Schubert | |
| 5,221,506 | A | 6/1993 | Dulin | |
| 6,171,007 | B1 | 1/2001 | Hsu | |
| 6,190,079 | B1 | 2/2001 | Ruff | |
| 6,280,750 | B1 | 8/2001 | Roulier et al. | |
| 6,491,937 | B1 * | 12/2002 | Slavtcheff et al. | 424/402 |
| 6,893,182 | B1 | 5/2005 | Liao | |
| 6,896,435 | B1 | 5/2005 | Rink | |
| 2003/0100236 | A1 | 5/2003 | Seth et al. | |
| 2003/0220212 | A1 | 11/2003 | DeVitis | |
| 2004/0033915 | A1 | 2/2004 | Aleles et al. | |
| 2004/0097385 | A1 | 5/2004 | Chen et al. | |
| 2004/0176002 | A1 * | 9/2004 | Siegwart | 442/35 |
| 2004/0254086 | A1 * | 12/2004 | Hedges et al. | 510/438 |
| 2005/0113270 | A1 | 5/2005 | Stockman et al. | |

FOREIGN PATENT DOCUMENTS

| | | |
|---|---|---|
| EP | 1 266 599 | 12/2002 |
| FR | 2 271 808 | 12/1975 |
| GB | 1 551 587 | 8/1979 |
| GB | 2 280 906 | 2/1995 |
| WO | 99/42548 | 8/1999 |
| WO | 01/08658 | 2/2001 |

OTHER PUBLICATIONS

Grissett et al. U.S. Appl. No. 60/579,592 Jun. 14, 2004—Bar Soap With Fibrous Assembly.
Macedo et al. U.S. Appl. No. 60/579,465 Jun. 14, 2004—Packaged Fibrous Article and Process.
Int'l. Search Report No. PCT/EP 2005/006075 dated Dec. 19, 2005—3 pp.

* cited by examiner

*Primary Examiner*—Necholus Ogden, Jr.
(74) *Attorney, Agent, or Firm*—Michael P. Aronson

(57) ABSTRACT

An article that is especially suitable for cleansing skin is described which includes a foamable composition having the form of an elastic semi-solid gel and a fibrous layer made up of a continuous network of bonded fibers. The weight ratio of the foamable composition to the fibrous layer is in the range from about 30 to 1 to about 2000 to 1 and the foamable composition at least partially encompasses the fibrous layer.

11 Claims, No Drawings

FIBROUS ELASTIC GEL CLEANSING ARTICLE

This application claims the benefit of U.S. Provisional Application No. 60/579,592 filed Jun. 14, 2004.

FIELD OF INVENTION

The present invention is directed at cleansing articles which are composites of a fibrous layer that includes a continuous network of bonded fibers which is at least partially encompassed by a foamable composition in the form of an elastic semi-solid gel.

BACKGROUND OF INVENTION

Consumers have been increasingly receptive to new personal washing systems that provide better skin care, greater refreshment or that generally led to a more pleasurable bathing and showering experience. Although toilet bars are still widely used because of their convenient form and simplicity, liquid products and more recently sheets have grown in popularity.

Consumers recognize that liquids provide excellent skin care and fragrance attributes. However, this product form does not lather well without the use of an implement such as a sponge or so-called pouf and without such an implement, liquids are not perceived as economical. Sheets in contrast, lather well but are generally single-usage forms and thus are primarily used in facial washing where the perceived benefits more readily justifies their higher cost.

Liquid and sheet personal washing forms have primarily been targeted to female consumers, and these forms are not so widely used by men who often prefer bars for their convenience and refreshment qualities.

Based on extensive research, the inventors have discovered a new cleansing form, namely a resilient composite composed of a foamable elastic semi-solid gel that at least partially encompasses a fibrous layer formed from a continuous network of bonded fibers. The foamable gel utilizes gelling agents that are either thermo-reversible or triggered to set by changes in environment and permits the use of a range of surfactants especially those that have heretofore been only suitable for liquids because of their high solubility in water.

These composites have the advantage that they can provide the benefits of a liquid, e.g., mildness and fragrance impact, with the simplicity and economical usage of a bar. Furthermore, the resilient composites can be manufactured in a variety of shapes including those of a traditional toilet bar and thus are appealing to male consumers. Surprisingly, the combination of the different sensory stimuli provided by the elastic semi-solid gel and fibrous layer has been found to be highly appealing to may consumers.

These and other advantages of the compositions disclosed herein will become clear from the description of the invention.

The following patents and publications have been considered:

U.S. Pat. No. 4,613,446 describes a plastic mesh pad or sponge containing a gelled cleaning composition including an alkali metal phosphate, a wetting agent, fatty acid soap, a chelating agent and a surfactant.

U.S. Pat No. 3,949,137 describes a gel-impregnated sponge composed of two layers: one layer is impregnated with a hardened gel material and one layer is an unimpregnated sponge.

U.S. Pat. No. 5,221,506 describes a bar soap having a sponge core which is revealed after the soap bar is reduced to a sliver, said sponge core providing support and preventing breakage of the sliver thus reducing wastage.

U.S. Pat Application Publication No. 2003/0220212 A1 describes bar soap reinforced with a reinforcement member such as a mesh to prolong the usage of the bar.

U.S. Pat. No. 6,190, 079 describes a scrubbing soap bar composed of vegetable oil and glycerin into which is partially imbedded a thin fine-mesh netting that serves as a feature to facilitate grasping and holding the bar.

U.S. Pat. No. 4,969,225 relates to a bathing and cleansing article in the form a scrub brush specifically made to contain or hold a bar of soap.

U.S. Pat. No. 4,190,550 describes a seamless fibrous, soap-filled pad in the form of an envelope that surrounds a solid soap, which is held in integral form by the entanglement of the fibers.

U.S. Pat Application Publication No. 2004/0033915 A1 relates to cleansing bars including a cleansing composition and a plurality of discrete elements (e.g., fibers) having a length to diameter ratio of from about 50 to 1 to about 100,000 to 1.

EP 1 266 599 A1 describes a solid cleanser holder composed of an apertured textured film surrounding a solid cleanser. The film reduces slip, exfoliates and enhances lather.

U.S. Pat. Nos. 4,328,131, 4,181,632, 4,207,198, and GB 1 551 587 describe several embodiments of elastic bars that include gelatin, one or more surfactants, and ingredients to manipulate the elastic properties of the composition (e.g., gel strength).

U.S. Pat. No. 6,280,750 describes a solid cosmetic composition used for topical application, e.g., a moisturizing stick, that includes gellan gum, at least one hydrocolloid and at least one fatty chain-including amphiphilic polymer.

GB 2 280 906 A describes a shaped toiletry product in the form of a gel that includes a gelling agent, preferably gelatin, water and at least one surfactant. Shaped, single-use bath gels, shampoos and shower gels are disclosed.

U.S. Pat Application Publication No. 2004/0097385 A1 describes viscoelastic cleansing gel compositions including anionic surfactant and a polysaccharide gelling agent. The gels are "jiggly" and are used to form shaped body washes and shampoos.

WO 99/42548 describes aqueous detergent compositions having an aqueous phase containing a foaming surfactant, a blend of kappa and iota carrageenan and water.

The present invention seeks improvements over deficiencies in the known art. Among the one or more problems addressed include developing a composite bar with excellent sensory properties, economy in use, mildness, and high lather.

SUMMARY OF THE INVENTION

The subject invention provides a cleansing article that is especially suitable for cleansing skin. The article is a composite of an aqueous foamable composition and a fibrous network of bonded fibers.

More specifically, the cleansing article includes:

i) a foamable composition that is an elastic, semi-solid gel, and ii) a fibrous layer comprising a continuous network of bonded fibers, wherein said fibrous layer is at least partially encompassed by said foamable composition and wherein the weight ratio of the foamable composition to the fibrous layer is in the range from about 30 to 1 to about 2000 to 1.

DETAILED DESCRIPTION OF THE INVENTION

As used herein % or wt % refers to percent by weight of an ingredient as compared to the total weight of the composition or component that is being discussed.

Except in the operating and comparative examples, or where otherwise explicitly indicated, all numbers in this description indicating amounts of material or conditions of reaction, physical properties of materials and/or use are to be understood as modified by the word "about." All amounts are by weight of the final composition, unless otherwise specified.

It should be noted that in specifying any range of concentration, any particular upper concentration could be associated with any particular lower concentration.

For the avoidance of doubt the word "comprising" is intended to mean "including" but not necessarily "consisting of" or "composed of." In other words, the listed steps or options need not be exhaustive.

The present invention relates to pliable and resilient cleansing articles composed of a foamable composition and a fibrous layer. The articles are primarily designed for multiple use by consumers. By the terms pliable and resilient is meant that the cleansing article can be readily deformed in the hands but can maintain its general shape and thus has a certain degree of springiness or sponginess. One benefit of pliability and resiliency is to facilitate a higher level of lather in a multi-use-cleansing article by allowing the fiber network to act a pump especially when the latter is also resilient. The degree of pliability and resiliency should be such that the cleansing article provides adequate lather and is judged to be aesthetically acceptable throughout the majority of its useful life.

The foamable composition, fibrous layer and methods to prepare and evaluate the compositions are described in detail below.

Foamable Composition

The foamable composition of the present invention is an elastic semi-solid gel. By the term elastic is meant that the composition substantially returns to its original shape after a force is applied for a set time and then removed. Specifically, the surface of the foamable composition when compressed to 80% of its thickness and held for 1 minute should be capable of returning to within about 5% of its original thickness within about 30 seconds.

The elasticity of the composition can be characterized by its elastic modulus, which is defined in the present context as the ratio of the force acting normal to a unit area of gel, and the linear displacement produced by this force. For soft gels, a more convenient measure is the compliance, which is the reciprocal of the elastic modulus, because it represents the extent of deformation produced by a unit stress (e.g., pressure) acting normal to the gel.

The compliance of the foamable composition are expressed as the displacement in millimeters produced by a 1 gram force acting over a 1 square centimeter area of gel. These compliance values in units of $mm/gm/cm^2$ can be converted into the SI units of M/Pa by multiplying by the factor $1.02\times10^{-4}$.

Since the compliance is a function of applied stress, a compliance at a stress value of 3.95 $gm/cm^2$ is a convenient measure for comparison of compositions as this represents the stress provided by a 20 gm force acting over 1 inch cylindrical platens (area 5.067 $cm^2$).

It has been found through experiments such as those described in Example 6 below, that the compliance should be in the range of from about 0.06 to about 1, preferably from about 0.07 to about 0.3 and most preferably from about 0.07 to about 0.2 $mm/gm/cm^2$ when measured at a stress value of 3.95 $gm/cm^2$ by the Instron Indentation Test described below in the EVALUATION METHODOLGY SECTION.

The term semi-solid as used herein designates structures that in the absence of a rigid container can keep the shape in which they have been molded or formed for long periods of time: typically days to months. However, they may easily be deformed (high compliance) and often exhibit viscoelastic behavior in shear deformation.

The term gel as used herein refers to a network formed through physical (including ionic) linkages that transforms a liquid, preferably aqueous, into an elastic semi-solid as opposed to covalent bond (chemical linkages) that form a permanent structure, e.g., a thermosetting polymer.

Another property that is useful in characterizing semi-solid gels is the yield stress (or maximum gel strength) expressed as the force per unit area required to cut or fracture the gel. Generally, the composition of the present invention have a yield stress that is greater than about 10 kPa, preferably greater than about 15 kPa and most preferably greater than about 20 kPa as measured by the Cheese Wire method described below in the EVALUATION METHODOLOGY SECTION.

Foamable compositions that have the above elastic and yield stress properties when combined with fibrous layers will form composites that have a yield stress between about 50 and 400 kPa, preferably between about 100 and about 350 kPa, and most preferably between about 150 and about 250 kPa when measured by the Cheese Wire method described below.

The foamable composition includes one or more gelling agents, surfactants and optional ingredients.

A. Gelling Agents

Gelling agents provide the main structuring of the foamable composition. Two main gelling agents are especially useful: thermo-reversible gelling agents and chemically triggered gelling agents.

Thermo-reversible Gelling Agent

A thermo-reversible gel is liquid at a temperature above the "melting point" of the gel, which is also described as the "sol-gel transition temperature". This liquid state is called the molten state or the sol state. Suitable gelling agents are those that produce an elastic semi-solid gel at a temperature below the "melting point" or "sol-gel transition temperature".

A preferred class of gelling agents is thermo-reversible gelling agents. These are polymers that are capable of forming a thermo-reversible gel in the presence of surfactants that are included in the foamable composition. By the term thermo-reversible is meant that the gel displays a transition from a gel state to a molten or sol state when heated above a certain temperature or temperature range. This melting point is characteristic of both the gelling agent employed and the overall composition. The melting point of the gel should be preferably above about 30° C., more preferably above about 35° C. and most preferably above about 40° C. Ideally, the melting point of the gel should be between about 40° C. and about 80° C., and most preferably between about 45° C. and about 70° C. so that it is stable over a broad range of temperatures that can be encountered in distribution yet be capable of economic manufacture at a reasonably low temperature.

Particularly suitable polymers are protein and polysaccharide biopolymers that are described in "Food Gels" (P. Harris—Ed, Elsevier Applied Science London and New York 1990) and in Industrial Gums, Polysaccharides and Their Derivatives" (R. L. Whistler and J. N. BeMiller—Eds, 3rd Edition, Academic Press, New York, 1993).

One suitable protein biopolymer for the present invention is gelatin, a complex mixture of collagen degradation products of molecular weight in the range of about 30,000 to about 80,000 and higher, depending on the hydrolytic conditions to which it has been subjected.

The gelatin employed is preferably colorless and free from odor. Gelatin is amphoteric (about 45 milliequivalents of amino functions and about 70 milliequivalents of carboxyl functions per hundred grams of polymer). It is normally used as a dry granular product, which is crystalline in appearance, although it is really amorphous. It is insoluble in cold water but swells rapidly in the presence of water until it has imbibed from about 6 to about 8 times its weight thereof and it melts to a viscous solution in water when warmed to 40 to 45° C. or more. Gelatins are classified as either Type A or Type B, the former being acid-derived, with an isoelectric point of from 8.3 to 8.5 and the latter being of alkali-derived, with an isoelectric point of from about 4.8 to about 5.0. Both types may be used, as may be mixtures of the two. Depending upon the ingredients present in the foamable composition and the pH, Type A or Type B may be preferable.

The gelling power of gelatin is normally measured by the Bloom Test, which is well known in the art. Viscosity can also be employed to characterize a gelatin and gel strength: viscosity ratio may be specified, e g, 3:1 30 to 5:1. Gel strengths will range from 100 to 300 g Bloom but will usually be in the range from or 200 to 300, with gelatins of Bloom values of 225 g and 300 g being especially suitable. The Type A gelatins will generally be utilized with the usual detergent constituents, normally intended for employment in neutral or slightly basic aqueous media and the Type B gelatins will be preferred when acidic conditions are expected to be encountered.

Examples of commercially available gelatins are available from CP Kelco, PB Leiner and FMC Biopolymer. Gelatins commercially available are both type A and B with Bloom strengths ranging from 175 to 300.

The level of gelatin used in the foamable composition is generally between about 5% and about 25%, preferably between about 7% and about 20% and most preferably between about 7.5% and about 15%.

Suitable polysaccharide gelling agents include carrageenans, gellan, and to a lesser extent agar and alginates.

Carrageenan is a class of polysaccharides, which occur, in red seaweed. They are linear polysaccharides made up of alternating beta-1,3- and alpha-1,4-linked galactose residues. The 1,4-linked residues are a D-enantiomer and sometimes occur as the 3,6-anhydride. Many of the galactose residues are sulfated.

A number of carrageenan structures have been described and commercial materials are available which approximate to the ideal structures. However, variations between these structures occur, depending on the source of the carrageenan and treatment of it after extraction.

A description of different carrageenan types is given in "Carrageenans" by Norman F Stanley which is Chapter 3 of "Food Gels" edited by Peter Harris, Elsevier, 1990.

Kappa carrageenan is sulfated on the 1,3-linked galactose residues, but not on the 1,4-linked residues. Iota carrageenan is sulfated on both residues. Lambda carrageenan has two sulfate groups on the 1,4-linked residues and one sulfate group on 70% of the 1,3-linked residues. Industrial treatment of lambda carrageenan with base can remove one sulfate group from some of the 1,4-linked residues: the resulting structure is designated theta carrageenan but does not occur naturally.

Commercially available kappa, iota and lambda carrageenan consists predominantly of material approximating the ideal structures mentioned above.

Aqueous solutions of kappa and iota carrageenan exist as gels. Lambda carrageenan on its own in aqueous solution does not form gels because its molecular structure prevents association between its molecules and consequent structuring in liquids.

In the instant invention preferably more than half of the carrageenan may be kappa or iota carrageenan or a mixture of the two. Mixtures of Kappa and Iota carrageenan are preferred as gelling agent compared to pure kappa carrageenan because it has been found that the mixtures are less prone to syneresis (exuding water) and shrinkage.

Lambda carrageenan may be used in mixtures with kappa and/or iota carrageenan but does not contain a continuous network of associated carrageenan molecules and thus is not suitable on its own.

Carrageenan is available from FMC-Biopolymer and from CP Kelco.

Gellan is another useful though less preferred polysaccharide gelling agent because it is less compatible with surfactants. Gellan is a microbial polysaccharide with tetrasaccharide repeat units that are composed of glucose, glucuronic acid, and rhamnose (2:1:1). Gellan is thus negatively charged depending upon pH.

Gellan is available from CP Kelco under the trade name KELCOGEL

Locust bean gum is another useful polysaccharide gelling agent especially in combination with carrageenan.

The total level of polysaccharide gelling agent, e.g., carrageenan and gellan, used in the foamable composition is generally between about 1% and about 10%, preferably between about 1.5% and about 7% and most preferably between about 2% and about 5%.

Combinations of protein and polysaccharide based gelling agents, e.g., gelatin with gellan or carrageenan, are also useful especially to extend the melting range of gelatin to higher temperatures.

The above discussion has focused on polymeric thermo reversible gelling agents. However, gelling agents that are colloidal in nature and whose colloidal interaction display thermal reversibility may also be acceptable if their properties are consistent with the intended application, e.g., are skin compatible and do not adversely effect mildness and lathering. Thus, colloidal particles with adsorbed polymers whose polarity depends on temperature concentrated dispersions that melt to form fluid emulsions, lyophilic sols and the like may be suitable. A key requirement however, is they display a melting behavior in the required temperature range, e.g., 30 C to 80 C, most preferably 40 C to 75 C.

Various auxiliary gelling agents can be used to increase the melting temperature of the gel or improve its properties. For gelatin, these auxiliary agents include sucrose and maltodextran (15% to 30%), modified starch, e.g., POLAR GEL—10 from American Maize, and hydroxy ethyl cellulose used alone or in combinations.

For Carrageenan, combinations with locust bean gums are useful both to modify gelling temperature but especially to reduce syneresis.

Monovalent, divalent and trivalent cations can act as cross-linking agents for the proteins and polysaccharides described above and thus are useful in increasing gel strength.

Useful monovalent cations include potassium and sodium ions as from the inclusion of potassium chloride or sodium chloride. Potassium ions are especially useful in combination with carrageenan.

Useful multivalent ions include calcium, magnesium, zinc and aluminum. Examples of soluble salts delivering these ions include chloride, bromide, acetate and sulfate salts such as potassium aluminum sulfate hydrate (alum), aluminum chloride, calcium chloride, magnesium sulfate, and zinc acetate.

Formaldehyde is still another material that can modify the gel strength especially of protein based gelling agents. About 0.1 to 1% of formaldehyde, preferably 0.1 to 0.3% in normally adequate.

Polyhydric alcohols can also be used as gel strength modifiers. These include sugars such as fructose, glucose, sucrose, sorbitol and lactitol as well as phenolic compounds such as 1,3-benzenediol, 1,2,4-benzenetriol, and 1,3,5-benzenetriol.

Denaturants can also be used as gel strength modifiers with protein based gelling agents. Examples of such materials include for example urea, guanidenehydrochloride, and dextrose.

Synthetic polymers have also been found useful in modifying gel strength. These include both water insoluble polymers such as the water insoluble resins sold by Arizona Chemicals under the UNICLEAR AND SYLVACLEAR trade name, and water soluble polymers such as cationic guars sold by Rhodia under the JAGUAR trade name. Other potentially useful synthetic polymers include polyacrylates, hydrolyzed polyvinyl acetate, and hydrophobically modified polyalkalene oxides, and modified cellulose, e.g., hydroxyethyl cellulose and starch.

Another group of auxiliary gelling agents are foaming surfactant that can form viscoelastic and thermo-reversible mesophases, i.e., liquid crystal phases such as the lamellar phase in 35° C. to 60° C. temperature range.

Chemically Triggered Gelling Agents

A second class of gelling agents are those whose sol to gel transition is sharply triggered by a change in chemical environment such as changes in pH, or concentration of other an ionic species such as zinc, calcium and borate ions.

Particularly suitable gelling agents of this type are acrylic acid and methacrylic acid containing polymers that are partially crosslinked by incorporation of multifunctional monomers. These polymers may also contain other free-radical polymerizable comonomers such as alkyl esters of acrylic and/or methyacrylic acid. Acid solutions of these polymers are generally free flowing low viscosity liquids (sol), which can be readily poured into a mold. However, when the sol is neutralized, the crosslinked polymers expand and can form a strong gel depending upon concentration and the presence of physical crosslinking agents.

Examples of acrylic acid polymers are the CARBOPOL polymers sold by NOVEON (especially CARBOPOL 934, 940, 941, and 956) as well as the hydrophobically modified variant PEMULEN (also from NOVEON), and the alkali swellable acrylic latex polymers sold by Rohm and Haas under the ARYSOL or ACULYN trade names.

Polyacrylamides and it's co- and ter-polymers with ethylenically unsaturated monomers such acrylic and methacrylic acid and their esters represent another class of gel forming polymers that can also be useful but are less preferred.

B. Surfactants

Synthetic Anionic Surfactants

The foamable composition of the present invention preferably contains one or more non-soap anionic detergents (syndets). Preferably the syndets have a zein value of 50 or less. Zein value may be measured using the test method described below. Advantageously non-soap anionic detergents or surfactants are used from about 3, 9 or 15% by wt. to about 9, 15 or 21% by wt.

The anionic surfactant may be an aliphatic sulfonate, such as a primary alkane (e.g., $C_8$-$C_{22}$) sulfonate, primary alkane (e.g., $C_8$-$C_{22}$) disulfonate, $C_8$-$C_{22}$ alkene sulfonate, $C_8$-$C_{22}$ hydroxyalkane sulfonate or alkyl glyceryl ether sulfonate (AGS); or an aromatic sulfonate such as alkyl benzene sulfonate.

The anionic may also be an alkyl sulfate (e.g., $C_{12}$-$C_{18}$ alkyl sulfate) or alkyl ether sulfate (including alkyl glyceryl ether sulfates) or a mixture of the two. Among the alkyl ether sulfates are those having the formula:

$RO(CH_2CH_2O)_nSO_3M$ wherein R is an alkyl or alkenyl having 8 to 18 carbons, preferably 12 to 18 carbons, and most preferably 12 to 14 carbons, n has an average value from about 1 to about 6, preferably about 1 to about 3; and M is a solubilizing cation such as sodium, potassium, ammonium or substituted ammonium (e.g., alkanolammonium). Ammonium and sodium lauryl sulfates, lauryl ether sulfates and their mixtures are one preferred type.

The anionic may also be alkyl sulfosuccinates (including mono- and dialkyl, e.g., $C_6$-$C_{22}$ sulfosuccinates); alkyl and acyl taurates, alkyl and acyl sarcosinates, fatty N-acyl amino acid salts, sulfoacetates, $C_8$-$C_{22}$ alkyl phosphates, alkyl phosphate esters and alkoxyl alkyl phosphate esters, acyl lactates, $C_8$-$C_{22}$ monoalkyl succinates and maleates, sulphoacetates, alkyl glucosides and acyl isethionates, and the like.

Sulfosuccinates may be monoalkyl sulfosuccinates having the formula:

$R^4O_2CCH_2CH(SO_3M)CO_2M$; and amide-MEA sulfosuccinates of the formula;

$R^4CONHCH_2CH_2O_2CCH_2CH(SO_3M)CO_2M$ wherein $R^4$ ranges from $C_8$-$C_{22}$ alkyl and M is a solubilizing cation.

Sodium and ammonium alkylethoxy (1-5 EO) sulfosuccinates, especially lauryl ethoxy (3 EO) sulfosuccinate are also useful.

Sarcosinates are generally indicated by the formula:

$R^1CON(CH_3)CH_2CO_2M$, wherein $R^1$ ranges from $C_8$-$C_{20}$ alkyl and M is a solubilizing cation.

Fatty N-acylamino acid salts of the general formula $$\begin{array}{l} R^1CONCHCO_2M, \\ \quad\quad\;\;| \\ \quad\quad R^5 \end{array}$$

where $R^5$ is the side chain of the amino acid, especially —H, —$CH_3$, —$CH_2COOH$.

Taurates are generally identified by the formula:

$$R^2CON(R^3)CH_2CH_2SO_3M$$

wherein $R^2$ ranges from $C_8$-$C_{20}$ alkyl, $R^3$ may be H or $C_1$-$C_4$ alkyl and M is a solubilizing cation.

The inventive skin care or foamable composition may contain $C_8$-$C_{14}$ acyl isethionates. These esters are prepared by reaction between alkali metal isethionate with mixed aliphatic fatty acids having from 6 to 12 carbon atoms and an iodine value of less than 20.

The acyl isethionate may be an alkoxylated isethionate such as is described in liardi et al., U.S. Pat. No. 5,393,466, titled "Fatty Acid Esters of Polyalkoxylated isethonic acid; issued Feb. 28, 1995; hereby incorporated by reference. This compound has the general formula:

$$R\ C—O(O)—CH(X)—CH_2—(OC(Y)H—CH_2)_m—SO_3M^+$$

wherein R is an alkyl group having 8 to 18 carbons, m is an integer from 1 to 4, X and Y are hydrogen or an alkyl group having 1 to 4 carbons and $M^+$ is a monovalent cation such as, for example, sodium, potassium or ammonium.

It has been found advantageous in some cases, especially with protein gelling agents that all or part of the cations of the anionic surfactants is nitrogenous. Preferably such cations include ammonium or mono-, di- and tri-alkanol ($C_1$-$C_3$) ammonium cations or a blend thereof.

The level of anionic surfactant is generally in the range from about 1% to about 20%, preferably from about-3% to about 15%, and most preferably from about 5% to about 15%.

Fatty Acid Soaps

Though less preferred than synthetic anionic surfactants, soluble soaps may optionally comprise 2-25%, preferably 2-10% by wt. of the foamable composition of the inventive article. Soluble soap is defined as a soap or soap blend having a Krafft point less than or equal to about 40° C. The soluble soap(s) can be selected from the chain length of $C_6$-$C_{14}$ saturated fatty acid soap(s) and $C_{16}$-$C_{18}$ unsaturated and polyunsaturated fatty acid soap(s) or a combination of these fatty acid soaps. Here the Krafft point of the soap is defined as the temperature at which the solubility of the soap rises sharply. These soluble soaps can be derived from coco fatty acid, Babasu fatty acid, palm kernel fatty acid and any other source of unsaturated fatty acid including tallow and vegetable oils and their mixtures. The soap may be prepared from coconut oils in which case the fatty acid content of C12-C18 is about 85%. In addition to specific "soluble" soap, additional soap(s), which may not be as soluble, may be used. These soap components are here referred to as insoluble soaps. The insoluble soap components can be in the range of 5-20% as structurant for the foamable composition of the inventive article.

The term "soap" is used here in its popular sense, i.e., the alkali metal or alkanol ammonium salts of aliphatic alkane- or alkene monocarboxylic acids. Sodium, potassium, mono-, di- and tri-ethanol ammonium cations, or combinations thereof, are suitable for purposes of this invention. In general, sodium soaps are used in the compositions of this invention, but from about 1% to about 25% of the soap may be potassium soaps. Overall the soap(s) useful herein are the well known alkali metal salts of natural of synthetic aliphatic (alkanoic or alkenoic) acids having about 12 to 22 carbon atoms, preferably about 12 to about 18 carbon atoms. They may be described as alkali metal carboxylates of hydrocarbons having about 12 to about 22 carbon atoms. The soaps may contain unsaturation in accordance with commercially acceptable standards. Excessive unsaturation is normally avoided to minimize the color and odor issues.

Soaps may be made by the classic kettle boiling process or modern continuous soap manufacturing processes wherein natural fats and oils such as tallow or coconut oil or their equivalents are saponified with an alkali metal hydroxide using procedures well known to those skilled in the art. Alternatively, the soaps may be made by neutralizing fatty acids, such as lauric (C 12), myristic (C 14), palmitic (C 16), or stearic (C 18) acids with an alkali metal hydroxide or carbonate.

Amphoteric Surfactants

One or more amphoteric surfactants may be used in this invention. Such surfactants include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

$$R^1—[—C(O)—NH\ (CH_2)_n—]_m—N^+—(R^2)(R^3)X—Y$$

where $R^1$ is alkyl or alkenyl of 7 to 18 carbon atoms;

$R^2$ and $R^3$ are each independently alkyl, hydroxyalkyl or carboxyalkyl of 1 to 3 carbon atoms;

n is 2 to 4;

m is 0 to 1;

X is alkylene of 1 to 3 carbon atoms optionally substituted with hydroxyl, and

Y is —$CO_2$— or —$SO_3$—

Suitable amphoteric surfactants within the above general formula include simple betaines of formula:

$$R^1—N^+—(R^2)(R^3)CH_2CO_2^-$$

and amido betaines of formula:

$$R^1—CONH(CH_2)_n—N^+—(R^2)(R^3)CH_2CO_2^-$$

where n is 2 or 3.

In both formulae $R^1$, $R^2$ and $R^3$ are as defined previously. $R^1$ may in particular be a mixture of $C_{12}$ and $C_{14}$ alkyl groups derived from coconut oil so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula:

$$R^1—N^+—(R^2)(R^3)(CH_2)_3SO_3^-$$

or $$R^1—CONH(CH_2)_m—N^+—(R^2)(R^3)(CH_2)_3SO_3^-$$

where m is 2 or 3, or variants of these in which —$(CH_2)_3SO_3^-$ is replaced by $$—CH_2C(OH)(H)CH_2SO_3^-$$

In these formulae $R^1$, $R^2$ and $R^3$ are as discussed previously.

A preferred sulfobetaine is cocoamidopropyl hydroxy sultaine

Amphoacetates and diamphoacetates are also intended to be covered in the zwitterionic and/or amphoteric compounds which are used such as e.g., sodium lauroamphoacetate, sodium cocoamphoacetate, and blends thereof, and the like.

A preferred amphoteric surfactant is cocoamidoproyl betaine.

The level of amphoteric surfactant is generally in the range from about 1% to about 15%, preferably from about 1% to about 10%, and most preferably from about 1.5% to about 8%.

Nonionic Surfactants

One or more nonionic surfactants may also be used in foamable composition of the inventive article. When present, nonionic surfactants may be used at levels from 1% to about 20%, preferably about 3 to about 15% by wt.

The nonionics which may be used include the reaction products of compounds having a hydrophobic group and a reactive hydrogen atom, for example aliphatic alcohols, acids, amides or alkylphenols with alkylene oxides, especially ethylene oxide either alone or with propylene oxide. Specific nonionic detergent compounds are alkyl ($C_6$-$C_{22}$) phenol ethylene oxide condensates, the condensation products of aliphatic ($C_8$-$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxide, and the like.

The nonionic may also be a $C_{10}$ to $C_{16}$, preferably $C_{12}$ to $C_{14}$ fatty alkanol amide such as cocamide MEA. These nonionics are particularly effective foam boosting agents.

The nonionic can generally be present in an amount ranging from about 0.1% to about 8%, preferably from about 0.5% to about 6% and most preferably from about 0.5% to about 4%.

Cationic Surfactants

One or more cationic surfactants may also be used in the inventive foamable composition. Advantageously cationic surfactants are used from about 3 to about 17%, preferably about 3% to about 10% 5 or 7% by wt.

Examples of cationic detergents are the quaternary ammonium compounds such as alkyldimethylammonium halides Other suitable surfactants which may be used are described in U.S. Pat. No. 3,723,325 to Parran Jr. titled "Detergent Compositions Containing Particle Deposition Enhancing Agents" issued Mar. 27, 1973; and "Surface Active Agents and Detergents" (Vol. I & II) by Schwartz, Perry and Berch, both of which are also incorporated into the subject application by reference.

C. Water and Cosolvents

The foaming surfactant phases of the invention are aqueous or aqueous/cosolvent gels that contain from about 15% to about 80%, preferably from about 20% to about 70% and most preferably from about 25% to about 60% water or a mixture of water and cosolvent based on the weight of the lathering composition.

The term "cosolvent" is used herein to describe water-miscible organic solvents that the inventors have found to improve the pliability, the clarity, and/or the storage stability of the gel.

Preferred solvents are substantially miscible with water to at least about 85% and innocuous to the skin. One group of suitable cosolvents for use herein include $C_1$-$C_{10}$ mono- or polyhydric alcohols and their alkoxylated ethers. In these compounds, alcoholic residues containing 3 to 6 carbon atoms are particularly preferred. Examples of this group include isopropanol, n-propanol, butanol, propylene glycol, ethylene glycol monoethyl ether, hexylene glycol, glycerol, and mixtures thereof.

A second group of suitable cosolvents include polyalkylene oxides having a molecular weight below 1000 Daltons. These include polyethylene oxide, polypropylene oxide, and random or block copolymers of ethylene oxide and propylene oxide alone or also containing butylene oxide and/or a terminal alcohol group having 2-12 carbon atoms.

The cosolvent(s) may be present at a level of from 0 to about 40%, preferably from about 2 to about 25% and most preferably from about 5% to 15% based on the total weight of the lathering composition.

D. Optional Ingredients

Skin Conditioning Agents

Another optional component in the foamable composition according to the invention is a skin conditioning agent. Useful skin conditioning agents include silicone and non-silicone (e.g., hydrocarbon) oils and waxes, and cationic polymers.

Examples of silicones useful as skin conditioning agents include polydiorganosiloxanes, in particular polydimethylsiloxanes such as dimethicone and dimethiconol; silicone gums or resins; high refractive index silicones, amino functional silicones such as amodimethicone and aminofunctional copolymers of dimethicone and polyalkyleneoxide, and copolymers of polydiorganosiloxanes and polyalkylene oxide.

Emulsified silicones for use in the compositions of the invention will preferably have an average silicone droplet size ranging from about 0.1 μm to about 100 μm. Suitable silicone emulsions for use in the invention are also commercially available in a pre-emulsified form either as conventional or as microemulsions.

Although non-volatile silicones are preferred in the present composition, volatile silicone can also be employed.

Non-silicone conditioning materials include oily or fatty materials such as hydrocarbon oils, fatty esters and mixtures thereof.

Hydrocarbon oils include cyclic hydrocarbons, straight chain aliphatic hydrocarbons (saturated or unsaturated), and branched chain aliphatic hydrocarbons (saturated or unsaturated) containing about 12 to about 30 or more carbon atoms. Examples of suitable hydrocarbon oils include paraffin oil, mineral oil, petrolatum, and polybutenes. Particularly preferred hydrocarbon oils are the various grades of mineral oils, and petrolatum.

Suitable fatty esters are characterized by having at least 10 carbon atoms, and include esters with hydrocarbyl chains derived from fatty acids or alcohols, e.g., monocarboxylic acid esters, polyhydric alcohol esters, and di- and tricarboxylic acid esters.

Polyhydric alcohol esters such as alkylene glycol and polyalkylene glycol mono, di, and tri esters are also suitable for use in the instant compositions. Particularly preferred fatty esters are mono-, di- and triglycerides, more specifically the mono-, di-, and triesters of glycerol and long chain carboxylic acids such as C1-C22 carboxylic acids. A variety of these types of materials can be obtained from vegetable and animal fats and oils, such as coconut oil, castor oil, safflower oil, sunflower oil, cottonseed oil, corn oil, olive oil, almond oil, avocado oil, palm oil, sesame oil, peanut oil, lanolin, coriander seed oil, borage seed and soybean oil.

Cationic polymers are optionally employed to provide enhanced deposition of the non-volatile, water-insoluble silicone as well as conditioning benefits in their own right. The level of cationic polymer in the composition can be in the range from about 0.01 to about 2%, preferably from about 0.1 to about 0.6%, and most preferably from about 0.15 to about 0.45%.

Particularly suitable cationic conditioning and deposition polymers for use in the composition include polysaccharide polymers, such as cationic cellulose derivatives, cationic starch derivatives, and cationic guars.

Examples of cationic cellulose polymers are those available from Amerchol Corp. (Edison, N.J.,) in their POLYMER JR and LR series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose treated with lauryl dimethyl ammonium-substituted epoxide, referred to in the industry (CTFA) as Polyquaternium 24. These materials are available from Amerchol Corp. (Edison, N.J.,) under the trade name Polymer LM-200.

An especially preferred cationic polymer is cationic guar gum derivatives, such as guar hydroxypropyltrimonium chloride, specific examples of which include the JAGUAR series commercially available from Rhodia Corporation (e.g., JAGUAR EXCEL or JAGUAR C13S). Other suitable cationic polymers include quaternary nitrogen-containing cellulose ethers, some examples of which are described in U.S. Pat. No. 3,962,418, which description is incorporated herein by reference. Other suitable cationic polymers include copolymers of etherified cellulose, guar and starch, some examples of which are described in U.S. Pat. No. 3,958,581, which description is incorporated herein by reference.

Non limiting examples of suitable optional synthetic cationic polymers include copolymers of vinyl monomers having cationic protonated amine or quaternary ammonium functionality with water soluble spacer monomers such as acrylamide, methacrylamide, alkyl and dialkyl acrylamides, alkyl and dialkyl methacrylamides, alkyl acrylate, allyl methacrylate, vinyl caprolactone or vinyl pyrrolidone. Other suitable optional synthetic polymers include vinyl compounds substituted acrylic monomers; copolymers of 1-vinyl-2-pyrrolidone and 1-vinyl-3-methylimidazolium salt (e.g., chloride salt)

Aesthetic and Adjunct Ingredients

A wide variety of optional ingredients can be incorporated in the foamable composition provided they do not interfere with the gelling and in-use properties of the composition (e.g., lather amount and rate). These include but are not limited to: perfumes; pearlizing and opacifying agents such as higher fatty acids and alcohols, ethoxylated fatty acids, solid esters, nacreous "interference pigments" such as TiO2 coated micas; dyes and pigments; sensates such as menthol and ginger; preservatives such as dimethyloldimethylhydantoin (Glydant XL1000), parabens, sorbic acid and the like; anti-oxidants such as, for example, butylated hydroxytoluene (BHT); chelating agents such as salts of ethylene diamine tetra acetic acid (EDTA) and trisodium etridronate; emulsion stabilizers; auxiliary thickeners; buffering agents; and mixtures thereof.

One of the benefits provided by the articles of present invention is better fragrance delivery in use and especially to the skin (see also Example 7). To take maximum advantage of this benefit it has been found preferable to utilize the Type 2 and/or Type 3 perfume molecules in the composition as classified by Yang et al in U.S. Pat. No. 6,806,249 incorporated in its entirety herein by reference. According to Yang et al the various types of perfume molecules are distinguished by the different physico-chemical properties set forth below.

Classification of Perfume Molecules

| Perfume Type | Examples of Partition Coefficient φ (log φ) | Hydrophobicity | Examples of Volatility Constant K* | Volatility | Initial headspace | Burst upon dilution |
|---|---|---|---|---|---|---|
| Type 1 | 50 (1.7) | Low | 50 | High | Very high | No |
| Type 2 | 1000 (3) | High | 1 | Low | Very low | high |
| Type 3 | 1000 (3) | High | 250 | High | High | Medium |
| Type 4 | 50 (1.7) | Low | 1 | Low | Low | No |

Note
*K is generally measured in units of atmosphere.

Examples of Type 2 perfume molecules include but are not limited to allyl cyclohexane propionate, ambrettolide, Ambrox DL (dodecahydro-3a,6,6,9a-tetramethyl-naphtho [2,1-b]furan), amyl benzoate, amyl cinnamate, amyl cinnamic aldehyde, amyl salicylate, anethol, aurantiol, benzophenone, benzyl butyrate, benzyl iso-valerate, benzyl salicylate, cadinene, campylcyclohexal, cedrol, cedryl acetate, cinnamyl cinnamate, citronellyl acetate, citronellyl isobutyrate, citronellyl propionate, cuminic aldehyde, cyclohexylsalicylate, cyclamen aldehyde, cyclomyral, dihydro isojasmonate, diphenyl methane, diphenyl oxide, dodecanal, dodecalactone, ethylene brassylate, ethylmethyl phenylglycidate, ethyl undecylenate, exaltolide, Galoxilide® (1,3,4,6,7,8-hexhydro,4,6,6,7,8,8-hexamethyl-cyclopenta-γ-2-benzopyran), geranyl acetate, geranyl isobutyrate, hexadecanolide, hexenyl salicylate, hexyl cinnamic aldehyde, hexyl salicylate, α-ionone, β-ionone, γ-ionone, α-irone, isobutyl benzoate, isobutyl quinoline, Iso E Super® (7-acetyl, 1,2,3,4,5,6,7,8-octahydro, 1,1,6,7-tetramethyl napthalene), cis-jasmone, lilial, linalyl benzoate, 20 methoxy naphthaline, methyl cinnamate, methyl eugenol, methylionone, methyl linoleate, methyl linolenate, musk indanone, musk ketone, musk tibetine, myristicin, neryl acetate, δ-nonalactone, γ-nonalactone, patchouli alcohol, phantolide, phenylethyl benzoate, phenylethylphenylacetate, phenyl heptanol, phenyl hexanol, α-santalol, thibetolide, tonalid, δ-undecalactone, γ-undecalactone, vertenex, vetiveryl acetate, yara-yara and ylangene.

Type 3 perfume molecules include but are not limited allo-ocimene, allyl caproate, allyl heptoate, anisole, camphene, carvacrol, carvone, citral, citronellal, citronellol, citronellyl nitrile, coumarin, cyclohexyl ethylacetate, p-cymene, decanal, dihydromyrcenol, dihydromyrcenyl acetate, dimethyl octanol, ethyllinalool, ethylhexyl ketone, eucalyptol, fenchyl acetate, geraniol, gernyl formate, hexenyl isobutyrate, hexyl acetate, hexyl neopentanoate, heptanal, isobornyl acetate, isoeugenol, isomenthone, isononyl acetate, isononyl alcohol, isomenthol, isopulegol, limonene, linalool, linalyl acetate, menthyl acetate, methyl chavicol, methyl octyl acetaldehyde, myrcene, napthalene, nerol, neral, nonanal, 2-nonanone, nonyl acetate, octanol, octanal, α-pinene, β-pinene, rose oxide, α-terpinene, γ-terpinene, α-terpinenol, terpinolene, terpinyl acetate, tetrahydrolinalool, tetrahydromyrcenol, undecenal, veratrol, and verdox.

Skin Benefit Agents

A variety of optional ingredients can be incorporated into the compositions of the instant invention to promote skin health and condition. Potential benefit agents include but are not limited to: lipids such as cholesterol, ceramides, and pseudoceramides; humectants and hydrophilic skin conditioning agents such as glycerol, sorbitol, propylene glycol, and polyalkalene oxides polymers and resins; antimicrobial agents such as TRICLOSAN; sunscreens such as cinnamates; exfoliant particles such as polyethylene beads, walnut shells, apricot seeds, flower petals and seeds, and inorganics such as silica, and pumice; additional emollients (skin softening agents) such as long chain alcohols and waxes like lanolin; additional moisturizers; skin-toning agents; skin nutrients such as vitamins like Vitamin C, D and E and essential oils like bergamot, citrus unshiu, calamus, and the like; water soluble or insoluble extracts of avocado, grape, grapeseed, myrrh, cucumber, watercress, calendula, elder flower, geranium, linden blossom, amaranth, seaweed, gingko, ginseng, carrot; impatiens balsamina, camu camu, alpina leaf and other plant extracts, and mixtures thereof.

The foamable composition can also include a variety of active ingredients that provide additional skin benefits. Examples include anti-acne agents such as salicylic and resorcinol; sulfur-containing D and L amino acids and their derivatives and salts, particularly their N-acetyl derivatives; anti-wrinkle, anti-skin atrophy and skin repair actives such as vitamins (e.g., A, E and K), vitamin alkyl esters, minerals, magnesium, calcium, copper, zinc and other metallic components; retinoic acid and esters and derivatives such as retinal and retinol, vitamin B 3 compounds, alpha hydroxy acids, beta hydroxy acids, e.g. salicylic acid and derivatives thereof; skin soothing agents such as propionic and acetic acid derivatives, fenamic acid derivatives; artificial tanning agents such as dihydroxyacetone; tyrosine; tyrosine esters such as ethyl tyrosinate and glucose tyrosinate; skin lightening agents such as aloe extract and niacinamide, alpha-glyceryl-L-ascorbic acid, aminotyroxine, ammonium lactate, glycolic acid, hydroquinone, 4 hydroxyanisole, sebum stimulation agents such as bryonolic acid, dehydroepiandrosterone (DHEA) and orizano; sebum inhibitors such as aluminum hydroxy chloride, corticosteroids, dehydroacetic acid and its salts, dichlorophenyl imidazoldioxolan (available from Elubiol); anti-oxidant effects, protease inhibition; skin tightening agents such as terpolymers of vinylpyrrolidone, (meth)acrylic acid and a hydrophobic monomer comprised of long chain alkyl (meth)acrylates; anti-itch agents such as hydrocortisone, methdilizine and trimeprazine hair growth inhibition; 5-alpha reductase inhibitors; agents that enhance desquamation; anti-glycation agents and mixtures thereof.

These agents may be selected from water soluble active agents, oil soluble active agents, pharmaceutically-acceptable salts and mixtures thereof. The term "active agent" as used herein, means personal care actives which can be used to deliver a benefit to the skin and/or hair and which generally are not used to confer a skin conditioning benefit, such are delivered by emollients as defined above. The term "safe and effective amount" as used herein, means an amount of active agent high enough to modify the condition to be treated or to deliver the desired skin care benefit, but low enough to avoid serious side effects. The term "benefit," as used herein, means the therapeutic, prophylactic, and/or chronic benefits associated with treating a particular condition with one or more of the active agents described herein. What is a safe and effective amount of the active agent ingredient will vary with the specific active agent, the ability of the active to penetrate through the skin, the age, health condition, and skin condition of the user, and other like factors. Preferably the compositions of the present invention comprise from about 0.0001% to about 50%, more preferably from about 0.05% to about 25%, even more preferably 0.1% to about 10%, and most preferably 0.1% % to about 5%, by weight of the active agent component.

Fibrous Layer

The inventive cleansing article includes a layer composed of a non-woven material also called a "batting layer", having a length (i.e. the major axis) and width (i.e. the minor axis) oriented in the x-y plane and a height oriented along its z axis.

The inventive fibrous material is defined as a continuous fiber network or fibrous assembly containing a large number of fiber to fiber bonds. Such continuous networks of bonded fibers are achieved by using one or a combination of chemically or thermally bonding fibers prior to impregnation with the foamable composition. The fibrous or batting layer may advantageously have from about 0.25 to about 7 or more fiber to fiber bonds per cubic millimeter. Preferably, the fibrous layer has about 0.5 to 5 fiber to fiber bonds per cubic millimeter. Most preferably the fibrous layer has a minimum of about 1 to 3 fiber to fiber bonds per cubic millimeter number. Such fiber bonds may be quantified using art recognized or equivalent techniques such as the method described below.

Fibrous structures/assembly described herein are comprised of synthetic and/or natural fibers converted via conventional, well-known non-woven, woven or knit processing systems or combinations thereof into continuous fibrous structures/assemblies. Generally well known non-woven processing systems transform fibers and filaments directly into useful cohesive structures with adequate strength that are not manufactured via knitting or weaving. Useful synthetic fibers include but are not limited to polyethylene, polypropylene, polyester, low-melt polyester, viscose rayon, polylactic acid and polyamide and blends/combinations thereof and the like. Further examples of synthetic materials useful as components in the present invention include those selected from acetate fibers, acrylic fibers, cellulose ester fibers, and methacrylic fibers. Examples of some of these synthetic materials include acrylics such as Acrilan®, Creslan®, and the acrylonitrile-based fiber, Orion®; cellulose ester fibers such as cellulose acetate, Arnel®, and Acele®; polyamides such as Nylons (e.g., Nylon 6, Nylon 66, Nylon 610 and the like); polyesters such as Fortrel®, Kodel®, and the polyethylene terephthalate fibers, Dacron®.

Additionally synthetic fibers used herein can be described as staple and continuous filaments including any blend thereof. Non-limiting examples of natural materials useful in the fibrous assembly in the present invention are silk fibers, keratin fibers and cellulosic fibers. Non-limiting examples of keratin fibers include those selected from wool fibers, camel hair fibers, and the like. Non-limiting examples of cellulosic fibers include those selected from wood pulp fibers, cotton fibers, hemp fibers, jute fibers, flax fibers, viscose fibers (rayon) and mixtures thereof. Additionally fibers used herein may include multi-component fibers or combinations thereof. Useful fiber deniers included herein range from about 1 denier to 20 denier including any combinations within this range.

With respect to manufacturing methods for nonwovens useful in the present invention, fibers are separated, oriented and deposited on a forming or conveying surface. Methods used to arrange or manipulate fibers described herein into a fibrous assembly include but are not limited to carding/garnetting, airlay, wetlay, spunbond, meltblown, vertical lapping or any combination/iteration thereof and the like. Cohesion, strength and stability may be imparted into the fibrous assembly via a bonding mechanism that include but are not limited to needlepunching, stitch bonding, hydroentangling, chemical bonding and thermal bonding and any combination/iteration thereof and the like. Fibers that comprise a fibrous structure/assembly may also be used that are not chemically, and thermally bonded to one another to supplement the continuous bonded network of the inventive bar. Such structures that form a plurality of fiber to fiber contacts are all well suited for the present invention.

Fibrous Assembly Properties

Fibrous assemblies useful for the present invention can range in basis weight from about 25 g/m$^2$ to 1000 g/m$^2$ In particular, for suitable lather generation of the inventive cleansing article, fibrous assembly density and therefore porosity (P) are important. Porosity can be defined as the volume fraction of air to fibers within a given fibrous assembly. Porosity can be expressed using following equation:

$$P = \frac{\rho_f - \rho_w}{\rho_f},$$

where $\rho_f$ is fiber density (g/cm$^3$) and $\rho_w$ is nonwoven density (g/cm$^3$). Note that the fibrous assembly density is based on the apparent thickness of the fibrous assembly structure. Preferably, the fibrous assembly of the present invention should display porosity in the range of from about 0.95 to 0.9999.

Another advantageous material property is the resiliency of the fibrous assembly used in the present invention. Specifically, Percent Energy Loss is a desirable parameter as it describes the resilience of the substrates to an applied load. % Energy Loss is calculated as follows:

$$\%\ EnergyLoss = \left[\frac{J_T - J_R}{J_T}\right] * 100,$$

where $J_T$, is the Total Energy required to compress the fibrous assembly to a 100 gram load and $J_R$ is the Recovered Energy during one compression cycle (see Energy Loss Test Method described below). Lower energy loss is seen to correspond to a more resilient fibrous assembly. Preferably, fibrous assemblies of the current invention have percent energy loss values ranging from about 5% to 50%.

Another useful property of the batting layer is air permeability. Air permeability preferably is in the range of about 200 to 900 cubic ft/sq. ft/min (about 60 to about 275 m$^3$/m$^2$/min), more preferably of about 300-700 cubic ft/sq. ft/min (about 90 to about 212 m$^3$/m$^2$/min). Note that 1 cubic ft/sq. ft/min is equal to 0.304 m$^3$/m$^2$/min. Air permeability may be measured using the methodology described below Some preferred embodiments of useful fibrous or batting layers include vertical lapped nonwovens, which can be further described as having a given number of pleats per inch, i.e., pleats per ca 2.54 cm. In this regards, pleats per inch is defined as the number of folds present in a one inch of nonwoven. This can be measured by placing two marks one inch apart in the machine direction of the nonwoven. Subsequently, a count the number of folds between the two marks is taken. The resultant count is taken as the pleats per inch. A suitable high bulk corrugated nonwoven fabrics are described in U.S. Pat. No. 3,668,054 to Stumpf issued on Jun. 6, 1972; and U.S. Pat. No. 4,576,853 to Vaughn et al. Issued on Mar. 18, 1986; which are incorporated in their entirety by reference herein.

There are a variety of other ways that pleats can be arranged within the fibrous layer to enhance its resiliency and usefulness as illustrated below.

In one arrangement, the non-woven or woven fibrous network is a corrugated bulky fabric that has pleats oriented substantially perpendicularly to the x-y plane of the cleansing article. The x-y plane is defined as the plane of largest surface of the article, i.e., the surface that mainly comes in contact with the skin during cleansing. Preferably there should be about 1 to 6 pleats per inch, i.e., about 2.5 pleats per cm to about 15 pleats per cm. Generally, the pleats will adhere together either through the use of an adhesive or by entanglements.

In another arrangement the non-woven or woven fibrous network is a corrugated bulky fabric that has a plurality of discrete peaks. The peaks form a 3 dimensional pattern where the major axis of the peaks is substantially aligned with the z axis of the fabric, i.e., the axis that is oriented substantially perpendicularly to the x-y plane of the cleansing article. Preferably the number of peaks per square cm is in the range of about 0.25 to about 3 peaks per square cm. Again adhesive or entanglement is generally used to reinforce the corrugated structure.

In another corrugated arrangement, the bulky fabric has a polygonal regular or irregular 3 dimensional honeycomb-like structure of approximately cylindrical cells. Here the major axis of each cylindrical cell of the honeycomb-like is oriented substantially perpendicularly to the x-y plane of the cleansing article.

In yet another corrugated variant, the bulky fabric has a plurality of attached layers oriented substantially perpendicularly to the x-y plane of the cleansing article. Here the attached layers can be arranged in a arbitrary pattern composed of one or more of spiral, wavy or folded arrangement(s).

In the above discussion, the various types of pleats were adhered together to reinforce the structure. However, the adhesive bond need not be so permanent as to survive beyond the entire useful life of the cleansing article. In fact under some embodiments of the invention, it is desirable that the adhesive actually fails after a set number of cleansing events, e.g., 3-100 uses or "washes". After failure, the pleats or corrugations separate and the fibrous layer stretches out so as to provide a clear signal or indicia that the useful life of the article has been reached.

Manufacturing and Packing

The cleansing articles of the invention are preferably made by a melt and pour (also called "melt-cast") process in which the molten foamable composition is combined with and at least partially encompasses the fibrous layer and is then allowed to gel, i.e., by reducing the temperature to below the melting point of the gel.

This process can be carried out in several ways. In one preferred embodiment, the combining step is carried out in a single-use mold where the mold forms all or a part of the package in which the cleansing article is sold or even stored during use. A description follows.

Two broad types of single-use molds, well known in the art, can be employed. The first is made up of two or more individual parts that are preassembled (press fitted or glued) into a "unitary design" before filling it with the molten foamable composition. In this case, the fibrous layer can be inserted into the mold either before or after the mold is assembled. Here, the molten composition is injected or poured into the mold, and then the mold entry is sealed by either heat sealing or with a separate covering (e.g., a polymer film). Such a mold can be filled either along one of its edges or along its face.

The second type of single-use mold is a "blister pack" formed by shaping a polymer film (e.g., blow molding or stretching over a mandrill) into a cup-like structure. Here, the fibrous layer can be inserted into the mold before or after the molten foamable composition is added. Furthermore, the bottom of the cup can have either a protrusion or well that accommodates a part of the fibrous layer, or can have an elevated or depressed area that provides an indicia or logo to the cleansing article. Once the blister pack is filled with both the molten composition and fibrous layer, the pack is sealed and cooled (not necessarily in this order). The sealing is generally accomplished by covering with a polymer, paper or laminated film: sealing provided via some form of adhesive or by heat or pressure sealing.

Either the unitary design or blister pack mold can be subjected to lower temperature cooling to accelerate the setting of the gel. The cooling can be accomplished either in bulk storage (e.g., a refrigerator) or by passage through a cooling chamber such as a cooling tunnel. The single use mold can serve as the final package at point of sale and thus bears printing or a means for hanging or display. Alternatively, the mold can be further wrapped or cartoned.

A second suitable processing route employs a multiple-use mold wherein the cleansing article is formed and set (gelled) in the mold, released from the mold for further processing. In this case the mold is reused. A disposable mold can also be used to accomplish the same processing ends—the mold being discarded after the article is demolded. In any event, the molten foamable composition is added to the mold by gravity or pressure feeding (injection). The mold can be of such a shape and volume so as to form either a single cleansing article or it can be a tray, pan, or cylinder so as to form a loaf, log or billet that can be cut into individual articles. Alternatively, the mold can include two or more element that are joined before the foamable composition is introduced (e.g., by injection under pressure) and then separated after the composition has set to release the article. Such an "injection mold" can form either an individual cleansing article or a log or loaf that can be cut after demolding. The setting process can be accomplished continuously, for example by chilling the mold, or the molds can be stored for a suitable period of time in a chamber at any temperature below the melting or setting point of the composition and later the article can be demolded.

The fibrous layer can be inserted into the multiple-use mold before or after the molten foamable composition and the mold can also include a recessed area to accommodate part of the fibrous layer. Alternatively, the mold can be partially filled and the foamable composition partially set before the fibrous layer is introduced.

Once set, the cleansing article is demolded and further processed and packed. For example, the article can be further shaped (e.g., by cutting), wrapped in a film (e.g., shrink-wrapped), cartoned or any combination of such steps.

In either of the manufacturing methods described above, the foamable composition can be partially cooled, for example by means of an in-line heat exchanger before the composition is inserted into the mold and combined with the fibrous layer.

Evaluation Methodology

A. Lather Improvement Factor (LIF)

This test is used to assess how various fibrous assemblies incorporated within the cleansing article improve lather generation.

The lather generation apparatus used in this test employed an inclined plane covered by ½ inch bubble wrap (e.g., 3-3930 distributed by Uline Inc, Newark, N.J.). Water is allowed to flow by gravity over this "washboard-like" surface from a delivery funnel and simultaneously the test cleansing article is rubbed under standardized conditions against the bubble-wrap to generate lather. The lather flows down the bubble-wrap clad inclined plane and is collected in a separatory volumetric measuring funnel. In particular, the following procedure is carried out for the foamable gel composition without the fibrous assembly and for the composite article containing the fibrous assembly.

1 Pour 200 ml of 38° C.±2° C. water contained in delivery funnel at a rate of 5.26 ml/sec through a pipette on to the upper edge of bubble wrap fixed in position and supported on a fixed inclined plane at an angle of 45 degrees from level.

2 Simultaneously, while pouring water over bubble wrap, scrub the wetted bubble wrap with the cleansing article or foaming gel composition in an oscillatory fashion. Use approximately 15 cm strokes while applying a low level of force pressing the bar to the wrap (approximately ¼ lb.) with sufficient frequency so that 60-70 up and down strokes are completed before the 200 ml of water has passed over bubble wrap surface.

3 Pour an additional 100-ml of 38° C.±5° C. water on to the upper edge of bubble wrap used in step 2 to collect lather in volumetric separatory funnel while its stopcock is closed.

4 Slowly rotate the stopcock so as to release water from the bottom of separatory funnel. When all of the water is removed, close stopcock and read lather volume in ml.

Note: Bubble wrap should be replaced after 10 tests with a new sheet.

For each formula tested, report:

$L_{WO}$=Lather Volume without substrate (ml)

$L_W$=Lather Volume with Substrate (ml)

LIF=Lather Improvement Factor, Calculated as follows

The LIF is calculated from the following equation:

$$LIF = \frac{L_W}{L_{WO}}$$

B. Percent Energy Loss Test Procedure:

Percent Energy Loss describes the resilience of a fibrous layer or substrate to an applied load. A 3.8 cm circular disk of the test fibrous layer is placed between the platens of an Instron Tensile/Compression Testing Machine (e.g. Instron Model No 4501 with load cell (226.98 N load Cell). The platen separation is 31.75 mm. The sample is then compressed at a compression cycle strain rate of 38 mm/min to a maximum load of 100 gm-force (0.98N) using a 5N load cell. The platens are then separated at a recovery cycle strain rate of 38 mm/min. Total Energy required to compress a sample to 100 grams load, and the Recovered Energy from one compression cycle is determined. The % Energy Loss is then calculated as follows:

$$\%\ EnergyLoss = \left[\frac{J_T - J_R}{J_T}\right] * 100$$

% Energy Loss is the resiliency of substrate i.e. the ability to recover compressive force $J_T$=Total Energy Required to Compress material to 100 grams $J_R$=Recovered Energy during one compression cycle C. Toilet Bar Yield Stress (Cheese Cutter) Method This method measures the yield stress of the semi-solid elastic gel and is a measure of the maximum gel strength. This method can also be used to measure the yield stress of the composition, i.e., the foamable composition that includes the fibrous layer.

A wire penetrating into cleansing material with a constant force will come to rest when the force on the wire due to internal stress balances the weight applied to the wire. The stress at the equilibrium point is described as yield stress ($\sigma_o$). The procedure is as follows.

A square of test sample (3.2 cm×3.2 cm×5 cm) is positioned on the yield stress device. A 400-grams weight is then attached to the arm of the device. The arm is then lowered such that the wire comes into contact with sample. The arm is then released allowing the wire to penetrate the test sample for 1 minute. The length of wire in the sample is then measured and recorded. The yield stress ($\sigma_o$) in kPa is determined from the following equation:

$$\sigma_o = \frac{0.375\ \text{mg}}{1D},$$

where, m=mass of driving wire (mass placed on device plus 56 grams)

g=gravitational constant (9.8 m/s$^2$

I=length of wire measured to penetrate soap after 1 minute (mm)

D=diameter of wire (e.g., 0.336 mm)

D. Instron Indentation Test

This method is used to measure the compliance (linear displacement per unit of stress at a give stress value (force per unit area)) of the foamable composition. Softer compositions are those which have a greater compliance.

The compliance is computed from measurements of the depth of indentation (displacement) as a function of applied load of a rod into a "block" formed from the semi-solid elastic gel composition (or a composite that also includes the fibrous layer). The displacement as a function of load was measured using an Instron Model 4501 Universal Testing Instrument.

Two blocks (typically 3.2 cm×3.2 cm×5 cm) of each composition are prepared and equilibrated in an environmental chamber at 21° C. and 50% relative humidity prior to testing. A 2.54 cm diameter indenting plate coupled to the Instron is then pressed against each block at a rate of 25 mm/min and recorded the forces at 50 data points per minute until a compression force of 65 grams is reached. The data is then transformed into the displacement at 5, 10, 20, 30 and 50 grams force applied load. Each block is compressed six times at different locations on the block.

The compliance at each applied stress in computed from:

Stress=Load (gm-force)÷Area of identing plate (cm$^2$)

Compliance=Displacement of indenting plate (mm) ÷Stress (gm/cm$^2$)

E. Air Permeability Methodology

The Air Permeability is related to the amount of lather that can be generated by a particular fibrous layer. The Air Permeability is proportional to the density and amount of lather that a particular nonwoven material is capable of generating. The Air Permeability values of the present invention were determined using ASTM Method—Designation D 737-96.

Testing Components

1. Test head that provides a circular test area of 38.3 cm 2±0.3%;
2. Clamping system to secure test specimens;
3. A clamping ring that minimizes edge leakage;
4. Air flow controller providing a minimum pressure drop of 125 Pa (12.7 mm or 0.5 in. of water) across the specimen);
5. Pressure gauge or manometer having an accuracy of ±2%;
6. Flowmeter, volumetric counter or measuring aperture to measure air velocity through the test area in cm 3/s/cm 2 (ft 3/min/ft 2) with an accuracy of ±2%;
7. Calibration plate, or other means, with a known air permeability at the prescribed test pressure differential to verify the apparatus;
8. Means of calculating and displaying the required results, e.g., scales, digital display, and computer-driven systems; and
9. Cutting dies or templates, to cut substrate specimens having dimensions at least equal to the area of the clamping surfaces of the test apparatus.

The substrate samples are cut to the appropriate size (size of clamping surface) using a cutting die. The samples are then preconditioned at a standard temperature and humidity, 21° C. ±1° C. and 65±2% R.H. Once the samples are preconditioned, they are allowed to reach moisture equilibrium in the standard atmosphere. The test samples are carefully handled to avoid altering the natural state of the samples. They are then place in the test head of the test apparatus, and the test is performed as specified in the manufacturer's operating instructions. The tests are carried out using a water pressure differential of 125 Pa (12.7 mm or 0.5 in. of $H_2O$). The individual test sample results are recorded in $ft^3/min/ft^2$ (or 0.304 $m^3/m^2/min$ in metric units) These results represent the Air Permeabilities of the samples.

F. Fiber to Fiber Bond Determination

A 4 mm×25 mm×25 mm section of nonwoven sample is prepared and placed on glass slide and secured with tape (sample slide). A reference glass slide is prepared by placing a 1 mm×1 mm mark on a glass surface. Photomicrographs of the reference slide are taken at a 10×magnification and the length of mark on photo in mm is measured and recorded. Photograph (×5) of the sample slide are then taken under the microscope at 10×magnification. This is repeated for three other samples with each sample done in duplicate. The number of fiber to fiber bonds on each photo is then counted. Using a scale created from the reference slide, the actual area of each sample slide is determined. The number of fiber-to-fiber bonds is divided by the actual area ($mm^2$) and the results finally averaged to provide the Number of Fiber-to-Fiber Bonds/$mm^3$.

Each image can be expressed as a given volume V, using as a thickness one fiber diameter. Assuming perfect fiber packing and no air voids between fibers. Given a porosity (P), where porosity is the volume fraction of fiber to air in a given nonwoven sample, the number of contacts per cubic millimeter for a given nonwoven having porosity P can be calculated as follows.

The Image Volume (V) is given by:

$$\text{Volume } (V) = \text{image area } (mm^2) * \text{ fiber diameter}(mm)$$

The Number of Fiber to fiber bonds per $mm^3$ (TC) is calculated from:

$$TC = CP/V$$

where CP is the number of fiber to fiber bonds taken from sample image.

The actual number of fiber to fiber bonds (AC) is then determined from the following equation:

$$AC = TC * (1 - \text{Porosity})$$

G. Zein Solubility Assay

The foamable compositions of the inventive cleansing article preferably have zein solubility of under about 50, 40, 30, and most preferably under about 25 using the zein solubility method set forth below. The lower the zein score, the milder the product is considered to be. This method involves measuring the solubility of zein (corn protein) in solution as follows:

0.3 g of foamable composition and 29.7 g of water are mixed thoroughly. To this is added 1.5 g of zein, and mixed for 1 hour. The mixture is then centrifuged for 30 minutes at 3000 rpm. After centrifugation, the pellet is extracted, washed with water, and dried in a vacuum oven for 24 hours until substantially all the water has evaporated. The weight of the dried pellet is measured and percent zein solubilized is calculated using the following equation:

$$\% \text{ Zein solubilized} = 100 \times (1 - \text{weight of dried pellet}/1.5).$$

The % Zein is further described in the following references: E. Gotte, "Skin compatibility of tensides measured by their capacity for dissolving zein protein", Proc. IV International Congress of Surface Active Substances, Brussels, 1964, pp 83-90.

H. Cleansing Article Integrity

The term "article integrity" refers to the ability of the cleansing article to maintain its shape, to resist fracture and to wear away uniformly when it is flexed and combined with water under conditions of handling that are encountered in typical use by consumers.

Article integrity is assessed either by an expert grader in the lab or by a panel of graders who use the article in their normal showering routine. In the lab evaluation, the article is first wet with water and then used to wash the assessors hands and forearms (pre-wet with water) either for a set period of time, typically 2 minute or for a sufficient time so as to generate lather. The assessor flexes and rotates the article in the hands during the assessment. The article is then rinsed and allowed to dry on a draining rack and evaluated. The process is then repeated up to 5 times ensuring that the article is allowed to dry for at least one hour before repeat evaluations.

The integrity is assessed on the following 4-point scale.

| Article Integrity Rating | Description |
|---|---|
| 1 | Article is firm and elastic and does not fracture when flexed. Gelled composition wears away gradually without noticeable chunks being removed. Article retains its general shape after several uses |
| 2 | Article fractures when flexed. Some visible chunks are removed during use but majority of cleansing composition wears away gradually. Article retains shape after several uses. |
| 3 | Article is weakly elastic and its shape is poorly retained after several uses. Cleansing composition dissolves away quickly, with the article lasting only a limited number of uses. |
| 4 | Foaming composition does not produce a solid or semi-solid gel during chilling under the normal processing conditions and a clearly viscous liquid remains |

I. SPME Analysis of Fragrance Retention

Fragrance retention on skin was measured by Solid Phase Micro Extraction (SPME). A slurry of the test foamable composition was prepared by combining 0.5 g of the composition with 1 ml of deionized water in a sealed container and stirring the mixture at about 30 to 35° C. for 30 minutes.

The forearm of a test subject was prewet with water at a temperature of 32° C. after which the entire sample of the slurry was applied with a gloved hand and the slurry was worked into a lather by gentle rubbing for 30 sec. The arm was then rinses for 15 minutes and patted dry with soft absorbent paper.

A closed bulb shaped collection vessel (approximate dimensions 2 cm in diameter by 50 cm high) containing a Supelco SPME Fiber Assembly (30 μm DVB/Carboxen/PDMS) was secured in contact with the forearm and perfume in the head space was collected for 30 minutes. The procedure was repeated but after allowing the treated forearm to remain uncovered for 60 minutes.

The SPME fibers were analyzed by gas chromatography using an Agilant Technologies (formerly Hewlett Packard) Model 6890 with Mass Selective Detector Model 5973. A The column an Agilant Technologies number 19091S-433, HP-5MS, 5% Phenyl Methyl Siloxane, 30 m×0.25 mm ID with a 0.25 μm film thickness.

EXAMPLES

The following examples are shown as illustrations of the invention and are not intended in any way to limit its scope.

Example 1

This Example Illustrates the Function of the Fibrous Layer in Maintaining Physical Integrity of the Cleansing Article and in Improving Lather Two cleansing articles, one an example of the instant invention, designated Ex 1 and the second a comparative example, designated C1, were prepared. Both articles included the same foamable composition shown in Table 1. The thermo-reversible gelling agent in this case was gelatin. The foamable composition was prepared by mixing all the components except the gelatin at 65° C. The gelatin was then added and the composition mixed until it a uniform liquid.

The fibrous network used to form the cleansing article of Ex 1 was a 100% polyethylene terephthalate nonwoven, designated SF-3 (X-87), obtained from Structured Fibers Incorporated, Saltillo, Miss. The fibrous network is characterized by the parameters given in Table 1B.

To prepare the cleansing article EX 1, approximately 100-grams of the foamable composition of Table 1A in the molten state at temperatures ranging from 45° C. to 65° C. was poured onto the fibrous assembly of Table 1B contained in a mold. The cleansing component is poured at temperatures lower than the melting/degradation temperature of the polymer/fiber combination of the batting layer so as not to substantially deform or degrade the fibrous assembly. The resulting intimately blended cleansing component and fibrous assembly is cooled to about 15° C. at approx. 50% RH until solidified and the solidified article (bar shaped) was removed from the mold.

TABLE 1

Pliable Bar Composition used for Example 1

| Component | % |
|---|---|
| Deionized Water | 41.89 |
| Polyquaternium-10 | 0.1 |
| Sodium Chloride | 0.325 |
| Sodium Hydroxide 50% | 0.048 |
| Glycerin USP | 1.00 |
| Ammonium Lauryl Sulfate | 5.08 |
| Ammonium Laureth Sulfate 2EO (70%) | 3.97 |
| Cocamide MEA | 0.869 |
| PEG-5 Cocamide MEA | 0.4345 |
| Citric Acid | 0.078 |
| DMDM Hydantoin | 0.017 |
| Cocamidopropyl Betaine | 10.00 |
| Propylene Glycol USP | 0.283 |
| Deionized Water | 25.00 |
| Gelatin | 10.00 |
| Tetrasodium EDTA 39% | 0.05 |
| Dequest 2010 (EHDP) | 0.033 |
| Kathon CG | 0.02 |
| Fragrance | 0.8 |
| Color | 0.0025 |
| Total | 100 |

TABLE 1B

Characteristics of Non-woven fibrous assembly (SF-3) used in Ex 1

| Denier | % |
|---|---|
| 4 | 25 |
| 6 | 75 |
| Fiber Type | 100% PET |
| Basis Weight (oz/sq. yd)* | 5 |
| Number of fiber to fiber bonds per cubic mm | 2.19 |

Note
*Oz/sq. yd = 33.9 gm/m$^2$

The process for preparing comparative example C1 was identical to that used for Ex 1 except that the fibrous assembly was absent.

The cleansing articles so prepared were evaluated for yield stress, lather volume, lather enhancement factor, and overall in-use characteristics by the methods described above in the EVALUATION METHODOLOGY section. The results are collected in Table 1C.

TABLE 1C

Effect of fibrous layer on properties on cleansing articles

| | CLEANSING ARTICLE | |
|---|---|---|
| | Ex 1 | C 1 |
| CHARACTERISTIC | | |
| % Vol. of Nonwoven to Detergent Phase | 0.306 | 0 |
| Total amount of Nonwoven per Article, grams | 1.0 | 0 |
| Total Amount of foamable composition, grams | 100.0 | 100 |
| Ratio of foamable composition by Wt of Fibrous Assembly | 100 to 1 | — |
| EVALUATED PHYSICAL PROPERTIES | | |
| Yield stress of foamable composition of Table 1A, kPa | 23.0 | 23.0 |
| Yield stress of composite article | 216.8 | — |
| Lather Volume, ml | 236.7 | 160 |
| Lather Improvement Factor relative to C 1 | 1.47 | — |
| Bar integrity during use (3 point rating) | 1 | 2-3 |

It is seen from the results in Table 1C that the non-woven fibrous layer dramatically improves the integrity and longevity of the cleansing article as well as increasing its lather performance. Without the fibrous network, the article rapidly disintegrates during use by a combination of fracture and excessive erosion. Thus, the fibrous layer is not a passive element of the invention but rather makes the pliable cleansing article practical for multi-use applications.

Example 2

Influence of Yield Stress of Foamable Composition on Properties of Cleansing Article The foamable compositions Ex 2A-EX 2D, shown in Table 2A, were prepared by the methods described in Example 1. Cleansing articles were prepared by the casting process also described in Example 1 using the fibrous layer set forth in Table 1B.

The properties of the cleansing articles so prepared are summarized in Table 2B. When the yield stress of the foamable composition is too low as in Ex 2C, e.g., less than about 10 kPa, the cleansing article has insufficient structure to retain its shape. Conversely, as the yield stress increases, the lather volume increases to a maximum value (Ex 2B) and then drops off with further increase in network rigidity (Ex 2D). However, the exact upper level of gel strength depends to some extent on the overall composition and surfactant content of the foamable composition.

TABLE 2A

Foamable compositions used in Example 2

| COMPONENT (as 100% active) | Ex 2A | Ex 2B | Ex 2C | Ex 2D |
|---|---|---|---|---|
| | Wt % | | | |
| Polyquaternium-10 | 0 | 0.09 | 0.1 | 0.09 |
| Sodium Chloride | 0.33 | 0.33 | 0.33 | 0.33 |
| Sodium Hydroxide 50% | 0.05 | 0.05 | 0.05 | 0.05 |
| Glycerin USP | 15 | 15 | 1 | 15 |
| Ammonium Lauryl Sulfate | 9 | 5.63 | 5.1 | 5.1 |
| Ammonium Laureth Sulfate 2EO (70%) | 7.03 | 4.39 | 3.97 | 3.97 |
| Stearic Acid | | | 5.5 | |
| Cocamide MEA | 1.54 | 0.96 | 0.87 | 0.87 |
| PEG-5 Cocamide MEA | 0.77 | 0.48 | 0.43 | 0.43 |
| Citric Acid | 0.14 | 0.08 | 0.08 | 0.08 |
| DMDM Hydantoin | 0.031 | 0.02 | 0.02 | 0.02 |
| Cocamidopropyl Betaine | 8.2 | 7.0 | 3.0 | 3.6 |
| Propylene Glycol USP | | 0.28 | | |
| Gelatin 40 mesh Bloom 175 | | 10.0 | 5.0 | 12.0 |
| Gelatin Bloom 275 | 7.5 | | | |
| Tetrasodium EDTA 39% | 0.05 | 0.05 | 0.05 | 0.05 |
| Jaguar C13S | 0.22 | 0.1 | | 0.1 |
| Dequest 2010 (EHDP) | 0.03 | 0.03 | 0.03 | 0.03 |
| Kathon CG | 0.02 | 0.02 | 0.02 | 0.02 |
| Fragrance | 1.0 | 1.0 | 1.0 | 1.0 |
| Color | 0.8 | 0.8 | 0.8 | 0.8 |
| Water | to 100% | to 100% | to 100% | to 100% |

TABLE 2B

Properties of cleansing articles of Example 2

| | Ex 2A | Ex 2B | Ex 2C | Ex 2D |
|---|---|---|---|---|
| CHARACTERISTIC | | | | |
| % Vol. of Nonwoven to Detergent Phase | 0.306 | 0.306 | 0.306 | 0.306 |
| Total amount of Nonwoven per Article, grams | 1.0 | 1.0 | 1.0 | 1.0 |
| Total Amount of foamable composition, grams | 100.0 | 100.0 | 100.0 | 100.0 |
| Ratio of foamable composition by Weight of Fibrous Assembly | 100 to 1 | 100 to 1 | 100 to 1 | 100 to 1 |
| EVALUATED PHYSICAL PROPERTIES | | | | |
| Yield stress of foamable composition of Table 2A, kPa | 21.88 | 23.03 | <10 | 30.63 |
| Lather Volume, ml | 124 | 126 | NA | 110 |
| Bar integrity during use (3 point rating)[a] | 1 | 1 | 4 | 1 |
| Comments: | | | Gel too weak to retain shape | Lather drops off gel to strong for adequate erosion |

Note
[a]Article disintegrates in use so foam level is meaningless

Example 3

Influence of Surfactants on Gelling Properties of Foamable Composition

The example foamable compositions Ex 3 and comparative examples C3A and C3B shown in Table 3A were prepared by the methods described in Example 1. Cleansing articles were prepared by the casting process of Example 1 using the fibrous layer set forth in Table 1B.

The properties of the cleansing articles so prepared are summarized in Table 3B. The Ex 3 foamable composition that employed ammonium based surfactants produces a robust (high integrity score), resilient, yet pliable, cleansing article that had high lather volume. In contrast, foaming compositions that were based on sodium alkyl ether sulfate (C3A) or a mixture sodium alkyl sulfate and sodium alkyl ether sulfate (C3B) did not form a semi-solid composition that retained its shape under the same processing conditions but rather remained as a viscous liquid or at best a weak gel. The example illustrates the criticality of using ammonium based surfactants when gelatin is employed as a thermo-revisable gelling agent. The example also illustrates that the suitability and properties (thermo-reversibility) of the gelling agent can not be judged solely from its behavior in water but rather may depend strongly on the surfactant composition employed.

TABLE 3A

Foamable compositions used in Example 3

| COMPONENT (as 100% active) | Ex 3 | C3A | C3B |
|---|---|---|---|
| | | Wt % | |
| Polyquaternium-10 | 0.09 | 0.09 | 0.09 |
| Sodium Chloride | 0.33 | 0.33 | 0.33 |
| Sodium Hydroxide 50% | 0.02 | 0.05 | 0.02 |
| Glycerin USP | 15 | 15 | 15 |
| Ammonium Lauryl Sulfate | 5.63 | | |
| Ammonium Laureth Sulfate 2EO (70%) | 4.39 | | |
| Sodium lauryl ether sulfate (2EO) | | 12.86 | 8.88 |
| Sodium lauryl sulfate | | | 2.66 |
| Cocamide MEA | 0.96 | | 0.83 |
| PEG-5 Cocamide MEA | 0.48 | | |
| Citric Acid | 0.08 | | |
| DMDM Hydantoin | 0.02 | | |
| Cocamidopropyl Betaine | 7.0 | 10 | 10 |
| Propylene Glycol USP | 0.28 | | 0.28 |
| Gelatin 40 mesh Bloom 175 | 10.0 | 10.0 | 10.0 |
| Gelatin Bloom 275 | | | |
| Tetrasodium EDTA 39% | 0.05 | 0.05 | 0.05 |
| Jaguar C13S | 0.1 | | 0.1 |
| Dequest 2010 (EHDP) | 0.03 | 0.03 | 0.03 |
| Kathon CG | 0.02 | 0.02 | 0.02 |
| Fragrance | 1.0 | 1.0 | 1.0 |
| Color | 0.8 | 0.8 | 0.8 |
| Water | to 100% | to 100% | to 100% |

TABLE 3B

Properties of cleansing articles of Example 3

| | Ex 3 | C3A | C3B |
|---|---|---|---|
| CHARACTERISTIC | | | |
| % Vol. of Nonwoven to Detergent Phase | 0.306 | 0.306 | 0.306 |
| Total amount of Nonwoven per Article, grams | 1.0 | 1.0 | 1.0 |

TABLE 3B-continued

Properties of cleansing articles of Example 3

| | Ex 3 | C3A | C3B |
|---|---|---|---|
| Total Amount of Detergent Phase, grams | 100.0 | 100.0 | 100.0 |
| Ratio of Detergent Phase by Wt of Fibrous Assembly | 100 to 1 | 100 to 1 | 100 to 1 |
| EVALUATED PHYSICAL PROPERTIES | | | |
| Yield stress of foamable composition of Table 2A, kPa | 23.03 | NA | NA |
| Lather Volume, ml | 126 | NA | NA |
| Bar integrity during use (3 point rating as in Example 1) | 1 | 4 | 4 |
| Description cleansing article after processing | sets to elastic semi-solid that retains shape | does not set - remains viscous liquid | does not set - remains viscous liquid |

Example 4

Illustration of Use of Different Non-woven Fibrous Layers

The foamable composition set forth in Table 4A was used to prepare cleansing articles that employed the different non-woven layers identified in Table 4B. These non-woven layers differ in porosity and resiliency as defined by the methods described in the EVALUATION METHODOLOGY section. Individual cleansing articles were prepared by pouring the molten foamable composition into a mold that contained the non-woven layer and then solidifying the composition at about 15° C. as discussed in Example 1. The resulting cleansing articles, which all had a shape similar to a conventional soap bar, are characterized in Table 4C.

TABLE 4A

Foamable composition used in Example 4

| COMPONENT (as 100% active) | Ex 4A-Ex 4E Wt % |
|---|---|
| Sodium Chloride | 0.33 |
| Sodium Hydroxide 50% | 0.05 |
| Glycerin USP | 11.00 |
| Ammonium Lauryl Sulfate | 10.13 |
| Ammonium Laureth Sulfate 2EO (70%) | 7.91 |
| Cocamide MEA | 1.73 |
| PEG-5 Cocamide MEA | 0.86 |
| Citric Acid | 0.156 |
| DMDM Hydantoin | 0.035 |
| Cocamidopropyl Betaine | 10.0 |
| Polyethylene Glycol 6000 | 1.0 |
| Polyquaternium-55 | 0.50 |
| Sodium Glycinate | 1.0 |
| Gelatin Bloom 275 | 12.00 |
| Tetrasodium EDTA 39% | 0.05 |
| Jaguar C13S | 0.54 |
| Dequest 2010 (EHDP) | 0.03 |
| Kathon CG | 0.02 |
| Fragrance | 0.80 |
| Color | 0.04 |
| Water | To 100% |

TABLE 4B

Non-woven fabrics used in cleansing articles of Example 4

| | Non-Woven | | | |
|---|---|---|---|---|
| Designation | Supplier | Porosity | Resiliency % Energy Loss | Material of Construction |
| LP Den | Legget & Platt Salisbury, NC | 0.9835 | 39.8 | PET |
| CAR 3 | Carlee Corp. Northvale, NJ | 0.9970 | 41.85 | PET |
| Kimberly Clark | K-C Corp. Neenah, WI | 0.9943 | 42.12 | PET |
| SF3 | Structured Fibers Saltillo, MS | 0.9951 | 15.79 | PET |
| CAR 2 | Carlee Corp. Northvale, NJ | 0.9970 | 39.82 | PET |

TABLE 4C

Description of cleansing articles of Example 4

| | Ex 4A | Ex 4B | Ex 4C | Ex 4D | Ex 4E |
|---|---|---|---|---|---|
| Non-woven fibrous layer | LPDEN | CAR3 | KC | SF3 | CAR2 |
| Weight of foamable composition (Table 1) per cleansing article (gm) | 100 | 100 | 100 | 100 | 100 |
| Weight of non-woven (Table 4A) per cleansing article (gm) | 1 | 1 | 1 | 1 | 1 |
| Weight ratio of foamable composition to fibrous layer | 100 to 1 | 100 to 1 | 100 to 1 | 100 to 1 | 100 to 1 |
| EVALUATED PHYSICAL PROPERTIES | | | | | |
| Bar integrity during use (3 point rating as in Example 1) | 1 | 1 | 1 | 1 | 1 |
| Lather Volume, ml | 94 | 102.5 | 85 | 124 | 120 |
| Lather Improvement Factor (LIF) | 0.94 | 1.025 | 0.85 | 1.24 | 1.20 |

Incorporation of all of the non-woven materials resulted in a cleansing article that had good integrity and provided lather during use. However, the amount of lather improvement depended both on the porosity and the resiliency of the fibrous layer. In fact, the higher energy loss layers actually were detrimental to lather volume (Ex 4C)

The effect of resiliency of the fibrous substrate (e.g. nonwoven) was studied and was found to affect aesthetics when the inventive cleansing article is used to clean the skin. More resilient structures were found to maintain adequate dimensional stability over time and over larger number of uses compared to samples that have comparatively poorer resiliency. Specifically, the Percent Energy Loss appears to be an important parameter as it describes the resilience of the substrate to an applied load (see test method below). Lower energy loss corresponded to a more resilient fibrous substrate with better in-use properties.

Although all the above example were robust and provided lather, Example Ex 4D which displays the lowest % energy loss values and hence is the most resilient of the fibrous layers tested provided the highest lather score. This cleansing article made with a low energy-loss non-woven was highly appealing to consumers in panel tests because of its in-use aesthetics. Consequently fibrous substrates with high-energy loss (e.g., greater that about 25%) are relatively less preferred because they display relatively poorer resiliency and lather improvement.

Example 5

Cleansing Articles with Different Thermo-reversible Polymers

The foamable compositions set forth in Table 5A were prepared. The appropriate weight of polymer powder was added with stirring to deionized water and the mixture was heated to 90-100° C. for 1-3 hours. A concentrated solution of the surfactants (typically 25 wt %) was prepared in deionized water at 60-70° C. and salts were then added as required. The surfactant solution was added to the polymer solution.

Cleansing articles containing the fibrous layer SF-3 described in Table 1B were prepared by pouring each of the molten foamable cleansing compositions set forth in Table 5A into molds containing the non-woven fibrous layer, allowing the mold and contents to equilibrate overnight at ambient temperature and finally demolding the cleansing article. The articles so prepared had the general shape of a soap bar.

The properties of the articles so prepared are described in Table 5B. These thermo-reversible polysaccharides provided cleansing articles that had acceptable integrity during use. This example also illustrates that composite articles having good in-use properties can be made with relatively low levels of surfactant (10% in this case) relative to a bar which typically contains >50% surfactant by weight.

TABLE 5A

Foamable compositions used in Example 5

| Component | Ex 5A | Ex 5B Wt % | Ex 5C |
|---|---|---|---|
| Sodium lauryl ether (3EO) sulfate | 8.7 | 8.7 | 8.7 |
| Cocamidopropyl betaine | 1.3 | 1.3 | 1.3 |
| Disodium PEG5 lauryl citrate sulfosuccinate | | | |
| Kappa Carrageenan | 3.0 | 2.0 | 2.0 |
| Iota Carrageenan | | 0.6 | 0.6 |
| Potassium Chloride | | | 0.2 |

TABLE 5B

Properties of cleansing articles of example 5

| | Ex 5A | Ex 5B | Ex 5D |
|---|---|---|---|
| CHARACTERISTIC | | | |
| % Vol. of Nonwoven to Detergent Phase | 0.306 | 0.306 | 0.306 |
| Total amount of Nonwoven (SF-3 - Table 1) per Article, grams | 1.0 | 1.0 | 1.0 |
| Total Amount of Detergent Phase (as described in Table 5A), grams | 100.0 | 100.0 | 100.0 |
| Ratio of Detergent Phase by Wt of Fibrous Assembly | 100 to 1 | 100 to 1 | 100 to 1 |
| EVALUATED PHYSICAL PROPERTIES | | | |
| Yield stress of foamable composition of Table 1A, kPa | 28.89 | 19.26 | 19.63 |
| Lather Volume, ml | 98 | 106 | 96 |

TABLE 5B-continued

Properties of cleansing articles of example 5

| | Ex 5A | Ex 5B | Ex 5D |
|---|---|---|---|
| Lather Improvement Factor relative to the same composition without fibrous layer | 1.30 | 1.06 | 0.96 |
| Bar integrity during use (3 point rating) | 1 | 1 | 1 |

Example 6

Elastic Properties of Different Foamable Compositions

This example illustrates the criticality of the elastic properties of the foamable composition, as measured by the compliance and yield stress on the in-use properties of the composite cleansing article.

The foamable compositions whose compositions are recorded in Table 6A were prepared by the methods of Example 1. These compositions were all molded into block shapes of having the approximate dimensions: 3.2 cm×3.2 cm×5 cm by melt-casting in a suitable mold in the absence of the fibrous layer.

The extent of deformation (absolute strain) was measured as a function of applied load (stress) by the Instron Indentation Test described above. The compliance of each composition at several stress values was then computed. The results are shown in Table 6B. It is seen that the compositions span a range of compliance values.

The foamable compositions were also used to fabricate composite cleansing articles as in Example 1 using the SF3 non-woven material. The following observations were recorded.

Ex 6A: Although the composite article made for this composition (C=0.97 mm/(gm/cm$^2$) @ 3.95 (gm/cm$^2$)) remained intact, it is probably the softest "usable" composition for the cleansing composites of the invention.

Ex 6B and Ex 6C: Both composites made from these foamable compositions were much more robust than those that employed Ex 6A but were still to a bit too flexible, i.e., the foamable composition should preferably be less compliant.

Ex 6D: This composition provided composites with the best overall properties were well appreciated by consumers, and had an excellent balance of firmness and erosion rate.

Ex 6E: Composites formed from this composition although usable as a cleanser, were a bit too firm and did not erode as fast as Ex 6D so that there was a decrease in lather rate relative to Ex 6D.

It is seen from the above evaluation and Table 6B that the compliance of the foamable composition should be about 0.06 to about 1, preferably about 0.07 to about 0.3 and most preferably about 0.07 to about 0.2 mm/gm/cm$^2$ when measured at a stress value of 3.95 gm/cm$^2$.

TABLE 6A

Foamable compositions used in Example 6

| COMPONENT (as 100% active) | Ex 6A | Ex 6B | Ex 6C Wt % | Ex 6D | Ex 6E |
|---|---|---|---|---|---|
| Polyquaternium-10 | .10 | .10 | .09 | | |
| Sodium Chloride | 0.33 | 0.33 | 0.33 | 0.33 | 0.33 |

TABLE 6A-continued

| Foamable compositions used in Example 6 | | | | | |
|---|---|---|---|---|---|
| COMPONENT (as 100% active) | Ex 6A | Ex 6B | Ex 6C Wt % | Ex 6D | Ex 6E |
| Sodium Hydroxide 50% | 0.05 | 0.05 | 0.05 | 0.05 | 0.05 |
| Glycerin USP | 1.0 | 15 | 15 | 11 | 11 |
| Ammonium Lauryl Sulfate | 5.08 | 5.08 | 5.63 | 10.13 | 10.13 |
| Ammonium Laureth Sulfate 2EO (70%) | 3.97 | 3.97 | 4.39 | 7.91 | 7.91 |
| Stearic Acid | | | | | |
| Cocamide MEA | 0.87 | 0.87 | 0.96 | 1.731 | 1.731 |
| PEG-5 Cocamide MEA | 0.43 | 0.43 | 0.48 | 0.86 | 0.86 |
| Citric Acid | 0.078 | 0.078 | 0.08 | 0.156 | 0.156 |
| DMDM Hydantoin | 0.01 | 0.01 | 0.02 | 0.035 | 0.35 |
| Cocamidopropyl Betaine | 3 | 3.6 | 7 | 10 | 10 |
| Propylene Glycol USP | 0.28 | 0.28 | 0.28 | | |
| Gelatin 40 mesh Bloom 175 | 4.0 | 12.0 | 10.0 | | |
| Gelatin Bloom 275 | | | | 12.0 | 20.0 |
| Tetrasodium EDTA 39% | 0.05 | 0.05 | 0.05 | 0.05 | 0.05 |
| Jaguar C13S | 0.1 | 0.1 | 0.1 | 0.54 | 0.54 |
| Dequest 2010 (EHDP) | 0.03 | 0.03 | 0.03 | 0.03 | 0.03 |
| Kathon CG | 0.02 | 0.02 | 0.02 | 0.02 | 0.02 |
| Fragrance | 0.8 | 0.8 | 1.0 | 0.8 | 0.8 |
| Color | | | 0.8 | 0.04 | 0.04 |
| Polyethylene Glycol 6000 | | | | 1.0 | 1.0 |
| Sodium Glycinate | | | | 1.0 | |
| Polyquaternium-55 | | | | 0.5 | |
| Water | to 100% | to 100% | to 100% | to 100% | to 100% |

TABLE 6B

| Elastic modulus and yield stress of foamable compositions of Example 6 | | | | | |
|---|---|---|---|---|---|
| Sample Stress (gm/cm$^2$) | Ex 6A | Ex 6B | Ex 6C | Ex 6D | Ex 6E |
| | Compliance mm/(gm/cm$^2$) | | | | |
| 0.99 | 1.24 | 0.256 | 0.208 | 0.157 | 0.142 |
| 1.97 | 1.14 | 0.172 | 0.137 | 0.107 | 0.96 |
| 3.95 | 0.97 | 0.114 | 0.091 | 0.073 | 0.0646 |
| 5.92 | 0.83 | 0.091 | 0.0748 | 0.0583 | 0.0512 |
| 9.88 | 0.64 | 0.072 | 0.0643 | 0.0446 | 0.0379 |
| Yield Stress kPa | 30.63 | 23.03 | — | — | — |

Example 7

This Example Illustrates the Higher Fragrance of the Composite Articles

A composite cleansing article was produced by combining the composition shown in Table 7A with the SF3 non-woven material using the methods described in Example 1.

The perfume retention on forearms washed in a controlled manner with the Ex 7 cleansing article was measured by the SPME Analysis of Perfume Retention method described in EVALUATION METHODOLOGY SECTION.

The perfume retention by the SPME method was also measured of a comparative soap bar, C 4, that incorporated the same perfume at the same level as was used in Ex 7.

The perfume retention after 30 minutes measured on forearms washed with Ex 7 was 950 while retention on forearms washed with the soap bar was 550. Thus, after 30 minutes about 70% more perfume were retained. These differences are in the range found between typical liquid body washes and soap bars. Furthermore, perfume was still detectable on forearms washed with the composite bar even after an hour while essentially no fragrance was detectable by SPME in the case of the soap-washed forearms. These differences were self-perceivable at both time points.

Thus, the composite article of the invention provided a distinct perceivable benefit in terms of the fragrance retained on the forearm relative to a convention soap bar. Furthermore, the benefit is of a magnitude similar to that provided by a liquid body wash.

TABLE 7

| Composition of foamable composition used in Ex 7 | |
|---|---|
| COMPONENT (as 100% active) | Wt % |
| Sodium Chloride | 0.33 |
| Sodium Hydroxide 50% | 0.05 |
| Glycerin USP | 11.0 |
| Ammonium Lauryl Sulfate | 10.13 |
| Ammonium Laureth Sulfate 2EO (70%) | 7.91 |
| Cocamide MEA | 1.731 |
| PEG-5 Cocamide MEA | 0.86 |
| Citric Acid | 0.156 |
| DMDM Hydantoin | 0.035 |
| Cocamidopropyl Betaine | 10 |
| Polyethylene Glycol 6000 | 1.0 |
| Sodium Glycinate | 1.0 |
| Polyquaternium-55 | 0.5 |
| Gelatin Bloom 275 | 12.00 |
| Tetrasodium EDTA 39% | 0.05 |
| Jaguar C13S | 0.54 |
| Dequest 2010 (EHDP) | 0.03 |
| Kathon CG | 0.02 |
| Fragrance | 0.80 |
| Color | 0.04 |
| Water | To 100% |

Example 8

Foamable Compositions with Different Benefit Agents

This examples illustrates compositions with different sensory additives and skin benefits agents.

TABLE 8

| Example of different benefit agents of invention | | | | | | | |
|---|---|---|---|---|---|---|---|
| | Ex 8A | Ex 8B | Ex 8C | Ex 8D | Ex 8E | Ex 8F | Ex 8G |
| Ammonium Lauryl Sulfate | 5 | 10 | | | 10 | 10 | 10 |
| Ammonium Laureth Sulfate 2EO | 4 | 8 | 7 | 8 | 8 | 8 | 8 |
| Disodium Laureth Sulfosuccinate (3EO) | | | 5 | | | | |

TABLE 8-continued

Example of different benefit agents of invention

| | Ex 8A | Ex 8B | Ex 8C | Ex 8D | Ex 8E | Ex 8F | Ex 8G |
|---|---|---|---|---|---|---|---|
| Cocamide MEA | 1 | 2 | 0.5 | 0.5 | 2 | 2 | 2 |
| PEG-5 cocamide MEA | | 1 | | 0.5 | 1 | 1 | 1 |
| Cocamidopropyl Hydroxy Sultaine | | | | 4 | | | |
| Cocamidopropyl Betaine | 3 | 3 | 4 | 4 | 3 | 3 | 3 |
| Gellan | | | | | | 2 | |
| Carrageenan | | | | | 3 | 2 | |
| Gelatin Bloom 275 | 7.5 | 12 | 12 | 11 | 8 | 8 | 10 |
| Jaguar C13S | 0.2 | 0.6 | 0.1 | 0.1 | 0.5 | 0.2 | |
| Fragrance | 1 | 1 | 1 | 1 | | | |
| Color | 0.8 | 0.04 | 0.04 | 0.04 | 0.04 | 0.04 | 0.04 |
| Minors (preservatives, electrolytes, buffering agents) | 1 | 1 | 1 | 1 | 1 | 1 | 1 |
| Glycerin | 15 | 12 | 12 | 11 | 11 | 10 | 12 |
| Silicone emulsion (60,000 CST) | | | | | 5 | | |
| Frescolite | 0.5 | | | | | | |
| Wax fruit slices | | 1 | | | | | |
| Sunflower seed oil | | | | | 5 | 10 | 12 |
| Parcol MCX | | | | | | | 3 |
| Polyethylene beads | | 1 | | | | 2 | |
| Silica | | | | 3 | | | |
| Water | to 100% | to 100% | to 100% | to 100% | to 100% | to 100% | to 100% |

While this invention has been described with respect to particular embodiments thereof, it is apparent that numerous other forms and modifications of the invention will be obvious to those skilled in the art. The appended claims and this invention generally should be construed to cover all such obvious forms and modifications which are within the true spirit and scope of the present invention.

What is claimed is:

1. A cleansing article comprising:

i) a foamable composition comprising:

a) a foaming surfactant, b) from about 0.1 to about 20% of a thermo-reversible gelling agent having a melting temperature between about 30° C. and about 80° C., c) from about 20% to about 70% water wherein the foamable composition is a semi-solid elastic gel having a compliance of about 0.06 to about 1 $mm/gm/cm^2$ when measured at a stress value of 3.95 $gm/cm^2$ by the Instron Indentation Test; and ii) a fibrous layer comprising a continuous network of bonded fibers, have a porosity greater than about 0.95;

wherein the fibrous layer is a web comprised of fibers selected from polyethylene terephthalate, polyethylene, polypropylene, polyamide, cellulose, modified or regenerated cellulose and blends thereof, and is at least partially encompassed by the foamable composition and wherein the weight ratio of the foamable composition to the fibrous layer is in the range from about 30 to 1 to about 2000 to 1, and wherein the cleansing article has the shape of a toilet bar.

2. The cleansing article according to claim 1 wherein the thermo-reversible gelling agent is a polymer selected from proteins, polysaccharides and mixtures thereof.

3. The cleansing article according to claim 1 wherein the aqueous foamable composition comprises from about 0.1 to 50% of a surfactant selected from the group consisting of anionic surfactants, nonionic surfactants, amphoteric surfactants, cationic surfactants, and mixtures thereof.

4. The cleansing article according to claim 3 wherein the anionic surfactant contains cations of which at least about 50% of the cations are nitrogenous.

5. The cleansing article according to claim 1 wherein the aqueous foamable composition additionally comprises a gel strength modifying agent selected from the group consisting of mono-, di-, and tri-valent cations, synthetic or natural organic polymers, inorganic particles, and mixtures thereof.

6. The cleansing article according to claim 1 wherein the article has a lather improvement factor greater than 1.2.

7. The cleansing article according to claim 1 wherein the continuous network of bonded fibers has a Energy Loss of less than about 35%.

8. The cleansing article according to claim 1 further comprising an aesthetic ingredient selected from the group consisting of fragrances, colorants, pigments, cosmetics, suspended bodies or blends thereof; a skin conditioning ingredient is selected from hydrophobic emollients and hydrophilic emollients or blends thereof, and a skin active material is selected from anti-wrinkle ingredients, skin lightening ingredients, vitamins, antimicrobial ingredients, acne medications, exfoliating agents, astringent ingredients, antioxidant ingredients, enzymes, sunscreen ingredients, and blends thereof.

9. The cleansing article according to claim 1 wherein the fibrous layer is a 100% polyethylene terephthalate nonwoven bating layer.

10. The cleansing article according to claim 1 wherein the article is suitable for multiple use by consumers.

11. The cleansing article according to claim 1 wherein the aqueous foamable composition comprises from about 25% to about 60% water.

* * * * *